United States Patent
Chesbrough et al.

(10) Patent No.: US 8,131,346 B2
(45) Date of Patent: *Mar. 6, 2012

(54) APPARATUS AND METHOD FOR IMPLANTING A PRELOADED LOCALIZATION WIRE

(75) Inventors: Richard M. Chesbrough, Bloomfield Hills, MI (US); Steven E. Field, Grand Rapids, MI (US); Ryan L. Goosen, Coopersville, MI (US); Andrew R. Squires, Grand Rapids, MI (US); Ronald B. Peel, North Muskegon, MI (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 2266 days.

This patent is subject to a terminal disclaimer.

(21) Appl. No.: 10/707,043

(22) Filed: Nov. 17, 2003

(65) Prior Publication Data
US 2004/0122312 A1   Jun. 24, 2004

Related U.S. Application Data

(60) Provisional application No. 60/427,020, filed on Nov. 18, 2002, provisional application No. 60/427,024, filed on Nov. 18, 2002.

(51) Int. Cl.
 *A61M 25/00* (2006.01)
(52) U.S. Cl. ......... 600/435; 600/423; 600/424; 600/427
(58) Field of Classification Search .................. 600/423, 600/424, 427, 435
See application file for complete search history.

(56) References Cited

U.S. PATENT DOCUMENTS

| | | | |
|---|---|---|---|
| 2,907,327 A | 10/1959 | White | |
| 3,516,412 A | 6/1970 | Ackerman | |
| 4,103,690 A | 8/1978 | Harris | |
| 4,405,314 A | 9/1983 | Cope | |
| 4,582,061 A | 4/1986 | Fry | |
| 4,592,356 A | 6/1986 | Gutierrez | |
| 4,616,656 A | 10/1986 | Nicholson et al. | |
| 4,627,420 A | 12/1986 | Katz | |
| 4,634,432 A | 1/1987 | Kocak | |
| 4,747,831 A | 5/1988 | Kulli | |
| 4,799,495 A | 1/1989 | Hawkins et al. | |
| 4,874,376 A | 10/1989 | Hawkins, Jr. | |
| 4,909,250 A | 3/1990 | Smith | |
| 4,986,279 A | 1/1991 | O'Neill | |
| 5,057,114 A | 10/1991 | Wittich et al. | |
| 5,059,197 A | 10/1991 | Urie et al. | |
| 5,127,916 A * | 7/1992 | Spencer et al. | ............... 606/185 |
| 5,195,540 A | 3/1993 | Shiber | |
| 5,273,532 A * | 12/1993 | Niezink et al. | .................. 604/62 |

(Continued)

FOREIGN PATENT DOCUMENTS

EP   0385604 A2   9/1990

(Continued)

*Primary Examiner* — Long V. Le
*Assistant Examiner* — Ellsworth Weatherby

(57) ABSTRACT

An apparatus for percutaneously implanting a localization wire into a tissue mass comprises a cannula with a preloaded localization wire. An actuator is provided to effect the relative movement of the cannula and localization wire such that a distal end of the localization wire is exposed to the tissue mass. A method for implanting a localization wire includes inserting a cannula with a preloaded localization wire into a tissue mass and relatively moving the cannula and localization wire to expose a portion of the localization wire to the tissue mass.

54 Claims, 24 Drawing Sheets

U.S. PATENT DOCUMENTS

| | | | |
|---|---|---|---|
| 5,282,845 A | 2/1994 | Bush et al. | |
| 5,338,311 A | 8/1994 | Mahurkar | |
| 5,353,804 A | 10/1994 | Kornberg et al. | |
| 5,376,094 A | 12/1994 | Kline | |
| 5,417,708 A | 5/1995 | Hall et al. | |
| 5,534,007 A * | 7/1996 | St. Germain et al. | 623/1.11 |
| 5,542,915 A | 8/1996 | Edwards et al. | |
| 5,697,907 A | 12/1997 | Gaba | |
| 5,749,887 A | 5/1998 | Heske et al. | |
| 5,782,771 A | 7/1998 | Hussman | |
| 5,788,710 A | 8/1998 | Bates et al. | |
| 5,795,339 A | 8/1998 | Erskine | |
| 5,879,338 A | 3/1999 | Mahurkar | |
| 5,897,554 A | 4/1999 | Chia et al. | |
| 5,902,310 A | 5/1999 | Foerster et al. | |
| 5,954,655 A | 9/1999 | Hussman | |
| 5,954,670 A | 9/1999 | Baker | |
| 5,976,129 A | 11/1999 | Desai | |
| 6,053,925 A | 4/2000 | Barnhart | |
| 6,066,122 A | 5/2000 | Fisher | |
| 6,090,063 A * | 7/2000 | Makower et al. | 604/13 |
| 6,135,993 A | 10/2000 | Husman | |
| 6,156,013 A | 12/2000 | Mahurkar | |
| 6,161,034 A | 12/2000 | Burbank et al. | |
| 6,228,055 B1 | 5/2001 | Foerster et al. | |
| 6,241,665 B1 * | 6/2001 | Negus et al. | 600/374 |
| 6,261,302 B1 | 7/2001 | Voegele et al. | |
| 6,312,429 B1 | 11/2001 | Burbank et al. | |
| 6,336,904 B1 | 1/2002 | Nikolchev | |
| 6,340,367 B1 | 1/2002 | Stinson et al. | |
| 6,364,895 B1 | 4/2002 | Greenhalgh | |
| 6,371,904 B1 | 4/2002 | Sirimanne et al. | |
| 6,405,733 B1 | 6/2002 | Fogarty et al. | |
| 6,409,742 B1 | 6/2002 | Fulton, III et al. | |
| 6,427,081 B1 | 7/2002 | Burbank et al. | |
| 6,482,178 B1 | 11/2002 | Andrews et al. | |
| 6,540,693 B2 | 4/2003 | Burbank et al. | |
| 6,544,269 B2 | 4/2003 | Osborne et al. | |
| 6,547,762 B1 | 4/2003 | Botich et al. | |
| 6,564,806 B1 | 5/2003 | Fogarty et al. | |
| 6,567,689 B2 | 5/2003 | Burbank et al. | |
| 6,575,991 B1 | 6/2003 | Chesbrough et al. | |
| 6,582,402 B1 | 6/2003 | Erskine | |
| 6,638,234 B2 | 10/2003 | Burbank et al. | |
| 6,685,666 B1 | 2/2004 | Fontenot | |
| 6,716,179 B2 * | 4/2004 | Burbank et al. | 600/564 |
| 6,752,154 B2 | 6/2004 | Fogarty et al. | |
| 6,766,186 B1 | 7/2004 | Hoyns et al. | |
| 6,813,520 B2 * | 11/2004 | Truckai et al. | 607/101 |
| 6,824,527 B2 | 11/2004 | Gollobin | |
| 6,936,014 B2 | 8/2005 | Vetter et al. | |
| 6,951,564 B2 | 10/2005 | Espositio et al. | |
| 7,001,341 B2 | 2/2006 | Gellman et al. | |
| 7,044,957 B2 | 5/2006 | Foerster et al. | |
| 7,125,397 B2 | 10/2006 | Woehr et al. | |
| 7,424,320 B2 | 9/2008 | Chesbrough et al. | |
| 7,520,881 B2 | 4/2009 | Foushee et al. | |
| 2001/0003791 A1 * | 6/2001 | Burbank et al. | 600/431 |
| 2001/0023322 A1 | 9/2001 | Espositio et al. | |
| 2001/0034528 A1 * | 10/2001 | Foerster et al. | 606/116 |
| 2002/0019595 A1 | 2/2002 | Osborne et al. | |
| 2002/0052564 A1 | 5/2002 | Burbank et al. | |
| 2002/0077687 A1 | 6/2002 | Ahn | |
| 2002/0143359 A1 | 10/2002 | Fulton, III et al. | |
| 2002/0193815 A1 | 12/2002 | Foerster et al. | |
| 2003/0028236 A1 * | 2/2003 | Gillick et al. | 623/1.11 |
| 2003/0225420 A1 | 12/2003 | Wardle | |
| 2004/0049224 A1 | 3/2004 | Buehlmann et al. | |
| 2004/0073107 A1 | 4/2004 | Sioshansi et al. | |
| 2004/0106891 A1 | 6/2004 | Langan et al. | |
| 2004/0127765 A1 | 7/2004 | Seiler et al. | |
| 2004/0162574 A1 | 8/2004 | Viola | |
| 2005/0075606 A1 | 4/2005 | Botich et al. | |
| 2006/0074443 A1 | 4/2006 | Foerster et al. | |
| 2006/0111629 A1 | 5/2006 | Field et al. | |
| 2007/0021763 A1 | 1/2007 | Field et al. | |
| 2007/0021764 A1 | 1/2007 | Field et al. | |
| 2008/0033280 A1 | 2/2008 | Lubock et al. | |
| 2008/0097199 A1 | 4/2008 | Mullen | |

FOREIGN PATENT DOCUMENTS

| | | |
|---|---|---|
| EP | 0 393 972 | 10/1990 |
| EP | 0395997 A1 | 11/1990 |
| EP | 0 415 504 | 3/1991 |
| EP | 0481685 A1 | 4/1992 |
| EP | 0769280 A2 | 4/1997 |
| EP | 0769281 A2 | 4/1997 |
| EP | 0 937 443 | 8/1999 |
| EP | 1163888 A1 | 12/2001 |
| EP | 1 306 097 A1 | 5/2003 |
| EP | 1 317 938 A1 | 6/2003 |
| FR | 2 776 165 | 9/1999 |
| GB | 786 850 | 11/1957 |
| WO | 96/32892 A1 | 10/1996 |
| WO | 9908607 A1 | 2/1999 |
| WO | 0024320 A1 | 5/2000 |
| WO | 0024332 A1 | 5/2000 |
| WO | 2004045444 A2 | 6/2004 |

* cited by examiner

APPARATUS AND METHOD FOR IMPLANTING A PRELOADED LOCALIZATION WIRE

CROSS REFERENCE TO RELATED APPLICATION

This application claims the benefit of U.S. provisional application Ser. No. 60/427,020, filed Nov. 18, 2002, and U.S. provisional application Ser. No. 60/427,024, filed Nov. 18, 2002, both of which is incorporated herein in their entirety.

BACKGROUND OF THE INVENTION

1. Field of the Invention

In one aspect, the invention relates generally to an apparatus for implanting a localization wire and more particularly to an apparatus comprising a retractable cannula for implanting a preloaded localization wire. In another aspect, the invention relates generally to a method for implanting a localization wire and more particularly to a method for implanting a preloaded localization wire by retracting a cannula relative to the localization wire.

2. Description of the Related Art

Localization wires are common devices for marking non-palpable lesions in a tissue mass, usually breast tissue. When such a lesion is identified with a medical imaging technique, such as radiography and ultrasonography, it is often desirable to position a localization wire or other type of marker near the lesion to facilitate locating the lesion during later procedures, such as biopsy. Alternatively, a localization wire can be placed in the tissue mass after a biopsy has been taken. In this case, the localization wire marks the location of the biopsy cavity for future procedures, such as removal of the surrounding tissue or therapeutic treatment. It is critical that the localization wire is accurately implanted in the correct location. Localization wires, which typically comprise an anchor portion and a wire portion that extends from the anchor and through the skin surface, are especially effective for identifying lesions or biopsy sites because a practitioner can use the wire as a physical guide to the lesion rather than solely relying on imaging techniques. For the surgical excision of the lesion, the localization wire is the preferred way for the surgeon to locate the lesion.

To implant a localization wire, a needle is inserted into the tissue mass and, with guidance from imaging systems, the needle is positioned with its tip near a predetermined location. Once the needle is in place, the localization wire is manually threaded through the needle and inserted into the predetermined location. Thereafter, the needle is removed from the tissue mass, and the localization wire remains in place at the predetermined location. Alternatively, the needle is positioned with its tip at the predetermined location, the localization wire is manually advanced to the end of the needle, and the needle is manually withdrawn from the tissue mass. During either process, the wire can be inadvertently displaced from the predetermined location as the needle is removed. As a result, the localization wire can be positioned deeper or shallower than intended and, therefore, can inaccurately mark the predetermined location. Further, if ultrasonography is utilized for imaging, the procedure requires three hands: one to position the needle, a second to hold the ultrasonography transducer, and a third to feed the localization wire into the needle and tissue mass. If the three hands are not properly coordinated, then it can be difficult for the practitioner to accurately position the localization wire.

Devices containing preloaded wires have been developed to eliminate the need to thread the needle with the wire when the needle is inserted into the tissue mass. The localization wires of such devices can be implanted into the predetermined location by manual distal displacement of the localization wire. The practitioner can grasp the wire portion that extends from the proximal end of the needle and push the localization wire distally to insert the anchor portion into the tissue mass; however, this process still requires three hands. Alternatively, the device can comprise a plunger in operative communication with the localization wire. Displacement of the plunger into the needle forces the distal end of the localization wire past the tip of the needle and into the predetermined location. The force applied to the plunger can affect the final location of the localization wire. In order to correctly position the anchor, the practitioner must accurately place the tip of the needle a sufficient distance from the predetermined location and apply a suitable force to the plunger to displace the localization wire into the predetermined location.

There remains a desire amongst medical practitioners for a device that can accurately implant a localization wire and requires only a single hand, thus freeing the other hand to hold the imaging device. Such a device would make it possible for a single person to accurately place the localization wire.

SUMMARY OF THE INVENTION

An apparatus according to the invention for percutaneously implanting a localization wire within a tissue mass comprises a cannula defining a lumen and having a distal end forming an insertion tip, the cannula being moveable between an insertion position and an implant position; a localization wire located within the lumen and having a distal end near the insertion tip when the cannula is in the insertion position; and an actuator in operable communication with the cannula and operable between a charged condition and a discharged condition to effect the movement of the cannula between the insertion and implant positions by retracting the cannula relative to the localization wire. To implant the localization wire into the tissue mass, the cannula is inserted into the tissue mass and the actuator is placed in the discharged condition to retract the cannula from the insertion position to the implant position and expose the distal end of the localization wire to the tissue mass.

The insertion tip is sharpened to aid in the insertion of the cannula into the tissue mass.

The cannula further comprises at least one imageable portion, and the at least one imageable portion can comprise multiple spaced imageable portions.

The localization wire comprises at least one anchor for holding the localization wire in the tissue mass. The at least one anchor can comprise opposing anchors. The at least one anchor can be a barb, and the barb can be integrally formed with the localization wire. The localization wire can also comprise an imageable portion, and the imageable portion can comprise a change in contour of the wire.

The actuator comprises a biasing element coupled to the cannula to move the cannula from the insertion position to the implant position. The actuator further comprises a trigger operable between a ready position and a release position for controlling the operation of the biasing element. The biasing element is a spring in operable communication with the trigger such that movement of the trigger from the ready position to the release position releases the spring from a compressed state to an expanded state to move the cannula from the insertion position to the implant position.

The apparatus further comprises a handle defining a hollow interior and an end, with the cannula being slidably mounted to the end. The spring is located within the hollow interior and extends between the end and a collar extending from the cannula.

The trigger is pivotally mounted to the handle and includes a finger that abuts the collar when the trigger is in the ready position, and can be pivoted to the release position to remove the finger from abutting contact with the collar to release the spring.

The collar forms a key and the apparatus further comprises a keyway shaped for receiving the key, and wherein the key is unaligned from the keyway when the actuator is in the charged condition and is aligned with the keyway when the actuator is in the discharged condition. The trigger can be rotatably mounted to the handle and operably coupled to the key such that rotation of the trigger aligns the key with the keyway to thereby release the spring. The trigger can form the keyway and displacement of the trigger to the release position aligns the key with the keyway to thereby release the spring.

The localization wire is contained entirely within the cannula and the handle.

An apparatus according to the invention for percutaneously implanting a localization wire within a tissue mass, comprises a handle with a hollow interior and an end; a cannula defining a lumen and having a distal end forming an insertion tip, the cannula being slidably mounted to the end of the handle and moveable between an insertion position and an implant position; a localization wire located within the lumen and having a distal end near the insertion tip when the cannula is in the insertion position; and an actuator operable between a charged condition and a discharged condition to effect the movement of the cannula between the insertion and implant positions by retracting the cannula relative to the localization wire. The handle, the cannula, the localization wire, and the actuator form a self-contained implanting apparatus for implanting the localization wire into the tissue mass, whereby the cannula is inserted into the tissue mass and the actuator is placed in the discharged condition to retract the cannula from the insertion position to the implant position and expose the distal end of the localization wire to the tissue mass.

The actuator comprises a biasing element operably coupled to the cannula to move the cannula from the insertion position to the implant position. The actuator further comprises a trigger operable between a ready position and a release position for controlling the operation of the biasing element. The biasing element is a spring operably coupled to the trigger such that movement of the trigger from the ready position to the release position releases the spring from a compressed state to an expanded state to move the cannula from the insertion position to the implant position. The spring is located within the hollow interior and extends between the end and a collar extending from the cannula.

The trigger can be pivotally mounted to the handle and includes a finger that abuts the collar when the trigger is in the ready position, and can be pivoted to the release position to remove the finger from abutting contact with the collar to release the spring.

The collar forms a key and the apparatus further comprises a keyway shaped for receiving the key, and wherein the key is unaligned from the keyway when the actuator is in the charged condition and is aligned with the keyway when the actuator is in the discharged condition. The trigger can be rotatably mounted to the handle and operably coupled to the key such that rotation of the trigger aligns the key with the keyway to thereby release the spring. The trigger can form the keyway and displacement of the trigger to the release position aligns the key with the keyway to thereby release the spring.

The localization wire is contained entirely within the cannula and the housing. The localization wire comprises at least one anchor for holding the localization wire in the tissue mass. The at least one anchor can comprise opposing anchors. The at least one anchor can be a barb, and the barb can be integrally formed with the localization wire. The localization wire further comprises an imageable portion.

The cannula further comprises at least one imageable portion. The at least one imageable portion can comprise multiple spaced imageable portions. The insertion tip is sharpened to aid in the insertion of the cannula into the tissue mass.

A method according to the invention for percutaneously implanting a localization wire into a tissue mass comprises the steps of inserting a cannula with a pre-loaded localization wire into the tissue mass; and retracting the cannula relative to the localization wire to expose a portion of the localization wire to the tissue mass.

The retracting step comprises automatically retracting the cannula relative to the localization wire. The retracting step further comprises activating an actuator to effect the automatic retraction of the cannula. The retracting step comprises removing the cannula from the tissue mass.

The insertion step further comprises using an imaging system for locating one of the cannula and the localization wire. The insertion step comprises locating an insertion tip of the cannula at a predetermined location within the tissue mass. The insertion tip of the cannula can be located at a biopsy site. The insertion step comprises positioning an imageable portion on the cannula at a predetermined location within the tissue mass.

The method further comprises a step of locating an imageable portion of the localization wire at a predetermined location within the tissue mass. The imageable portion of the localization wire can be located at a biopsy site.

A method according to the invention for percutaneously implanting a localization wire into a tissue mass using an apparatus comprising a cannula defining a lumen and having a distal end forming an insertion tip; a localization wire pre-loaded within the lumen and having a distal end near the insertion tip; and an actuator connected to the cannula and operable between a charged condition and a discharged condition to retract the cannula relative to the localization wire, wherein the method comprises the steps of inserting the insertion tip of the cannula and the localization wire into the tissue mass; and retracting the cannula relative to the localization wire to expose a portion of the distal end of the localization wire to the tissue mass.

The retracting step comprises automatically retracting the cannula relative to the localization wire. The retracting step further comprises displacing a trigger on the actuator to release a biasing element operably coupled to the cannula and thereby automatically retract the cannula. The retracting step further comprises retracting the cannula into an end of a handle with a hollow interior. The retracting step comprises removing the cannula from the tissue mass.

The insertion step further comprises using an imaging system for locating one of the cannula and the localization wire in the tissue mass. The insertion step comprises locating the insertion tip of the cannula at a predetermined location within the tissue mass so that when the cannula is retracted, the localization wire is exposed to the predetermined location. The insertion step comprises locating the insertion tip of the cannula at a biopsy site such that upon retraction of the cannula, the localization wire is located at the biopsy site. The insertion step comprises positioning an imageable portion on the cannula at a predetermined location within the tissue mass.

The insertion step comprises positioning at least one anchor on the localization wire at a predetermined location within the tissue mass so that when the cannula is retracted, the at least one anchor is embedded into the tissue mass at the predetermined location. The method further comprises a step of locating an imageable portion of the localization wire at a predetermined location within the tissue mass. The imageable portion of the localization wire can be located at a biopsy site.

DESCRIPTION OF THE INVENTION

Figure 1:
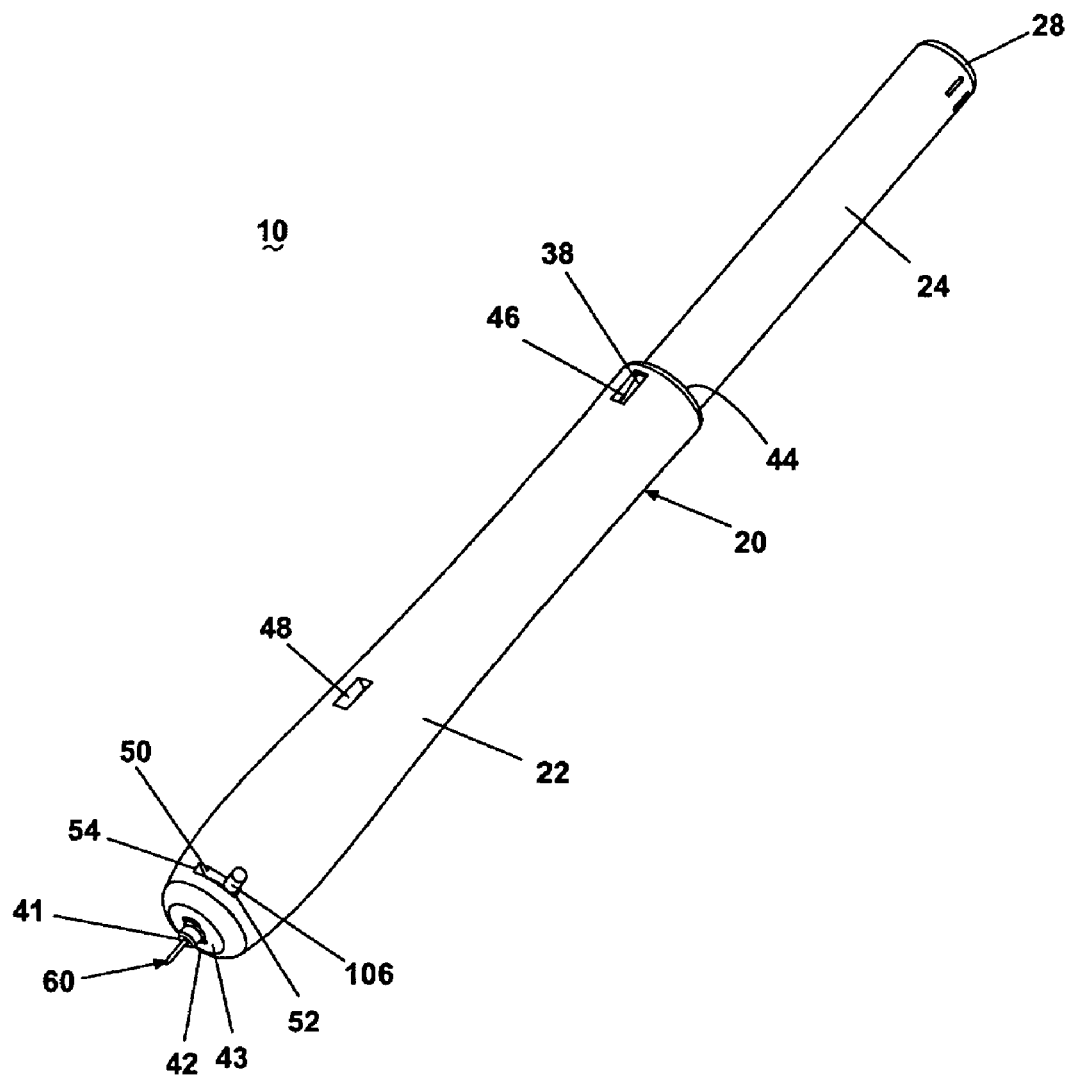
FIG. 1 is a perspective view of an apparatus for implanting a preloaded localization wire according to the invention, wherein the apparatus is shown in an uncocked condition.

The invention provides an apparatus for accurately implanting a localization wire within a tissue mass. The apparatus comprises a preloaded localization wire and a cannula that retracts proximally to expose the localization wire. Implantation of a localization wire with the apparatus requires only one hand.

Referring now to the figures, FIGS. 1-9 illustrate a first embodiment of a implanting apparatus 10 according to the invention, which is capable of the percutaneous placement of a localization wire at a predetermined location, such as a lesion or a biopsy site, within a tissue mass 150. The implanting apparatus 10 comprises a handle 20 for housing a cannula 60, a localization wire 80 partially contained within the cannula 60, and an actuator 90 for displacing the cannula 60 relative to the localization wire 80. It will become apparent in the following description that the handle 20, the cannula 60, the localization wire 80, and the actuator 90 form a self-contained implanting apparatus 10.

The handle 20 includes a grip portion 22 slidably mounted to a base portion 24 with a hollow interior 26, a closed proximal end 28, and an open distal end 30. The base portion 24 further comprises diametrically opposed L-shaped grooves 36 adjacent the hollow interior 26. Each groove 36, best viewed in FIG. 5, has a circumferential recess 34 that forms one leg of the L at the distal end 30 and a longitudinal keyway 32 that extends from an end of the circumferential recess 34 towards the proximal end 28 to form the other leg of the L. A pair of diametrically opposed resilient tabs 38 is located on the outside surface of the base portion 24 near the distal end 30.

The grip portion 22 defines a hollow interior 40 (FIG. 3) and comprises a distal end 42 with a wall 43 having an aperture 41 for slidably mounting the cannula 60 and an open proximal end 44 that receives the distal end 30 of the base portion 24. Further, the grip portion 22 includes first and second pairs 46 and 48 of diametrically opposed openings sized to receive the tabs 38. The first pair 46 of openings is located near the proximal end 44, and the second pair 48 are spaced from the first pair 46 at a distance less than the length of the base portion 24. A transverse slot 50 formed between first and second trigger arm stops 52 and 54 extends through the grip portion 22 near the distal end 48. The transverse slot 50 has an arc length substantially equal to that of the circumferential recess 34 of the groove 36.

Figure 2:
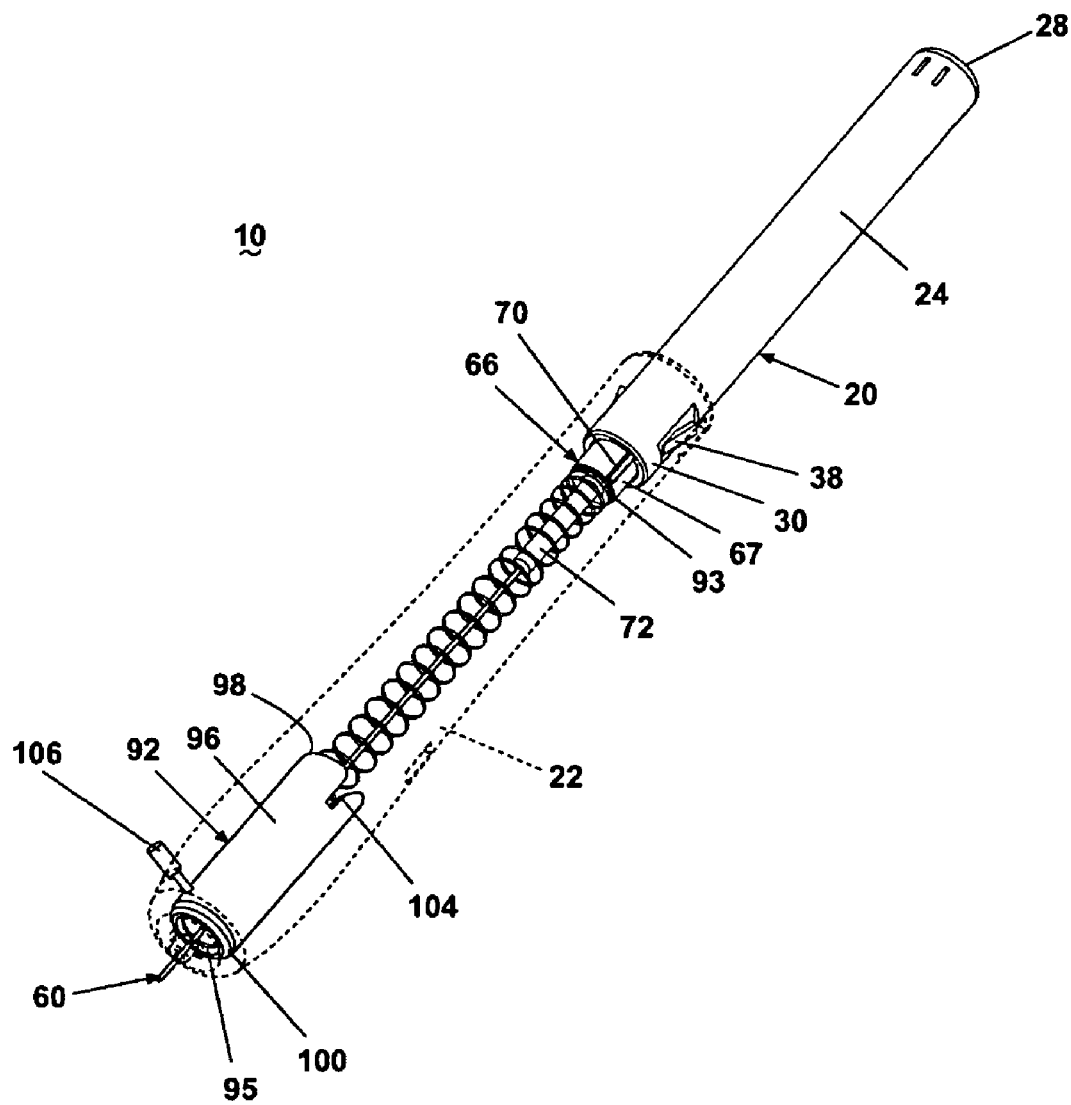
FIG. 2 is a perspective view identical to FIG. 1, wherein a grip portion is illustrated in phantom to show a spring-loaded cannula disposed inside the grip portion.
Figure 3:
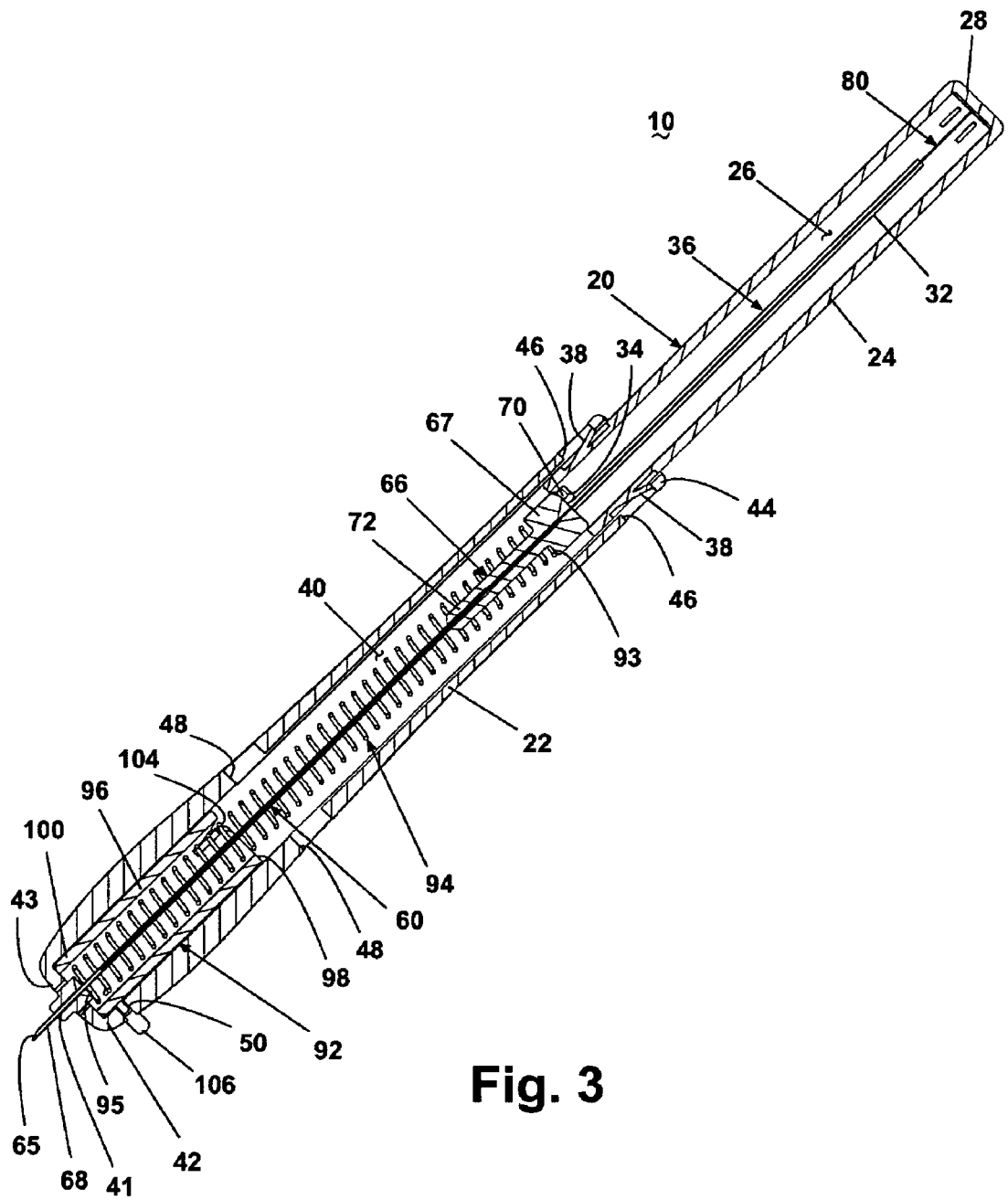
FIG. 3 is a sectional view of the apparatus in FIG. 1.
Figures 7, 7A:
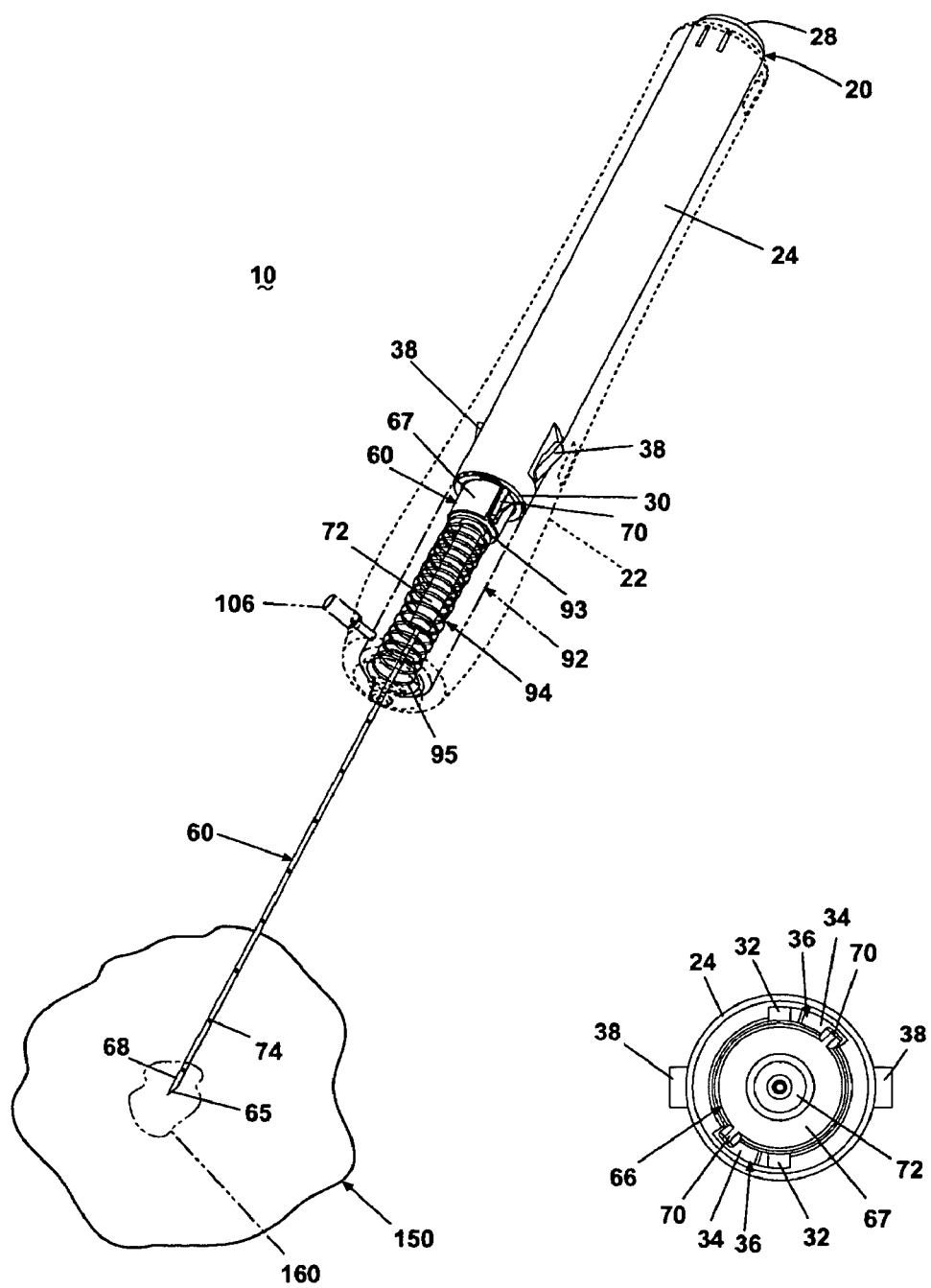
FIG. 7 is perspective view of the apparatus in FIG. 1 inserted into a predetermined location in a tissue mass, wherein the apparatus is in a cocked condition and the cannula is in an insertion position.
FIG. 7A is a front plan view of the key and keyway of the apparatus in FIG. 7, wherein the key and keyway are unaligned.

The handle 20 is slidable between an uncocked condition, as illustrated in FIGS. 1-3, and a cocked condition, as shown in FIG. 7. In the uncocked condition, the first pair 46 of openings receives the tabs 38, and the proximal end 44 of the grip portion 22 is near the distal end 30 of the base portion 24. In the cocked condition, the second pair 48 of openings receives the tabs 38, and the proximal end 44 of the grip portion 22 is near the proximal end 28 of the base portion 24. The interaction of the tabs 38 with the first and second pairs 46 and 48 of openings secures the handle 20 in the uncocked and cocked conditions, respectively. When the grip portion 22 slides from the uncocked condition to the cocked condition, distal displacement of the first pair 46 of openings deflects the resilient tabs 38 towards the base portion 24 such that the grip portion 22 can slide over the tabs 38 until the second pair 48 of openings aligns with and receives the tabs 38.

Figure 4:
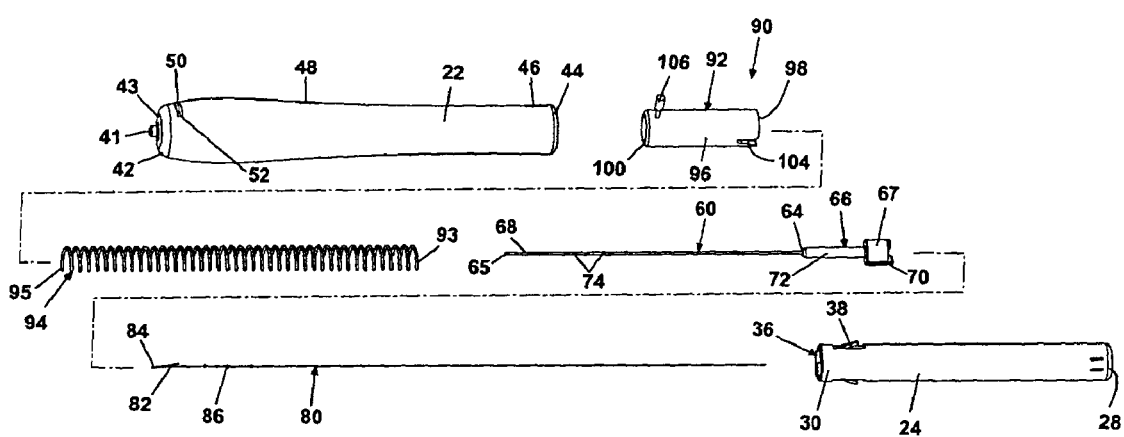
FIG. 4 is an exploded view of the apparatus in FIG. 1.
Figure 5:
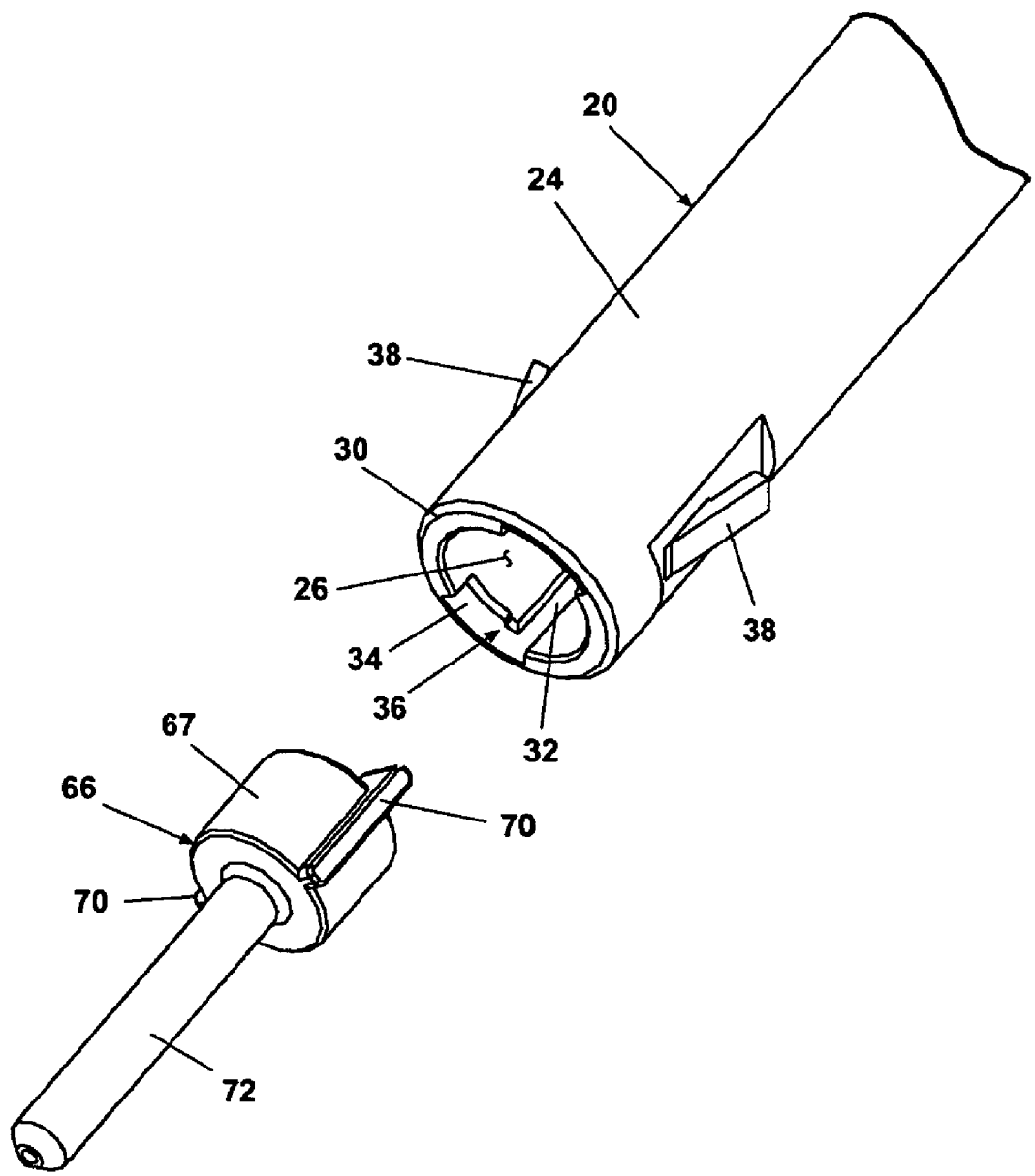
FIG. 5 is an enlarged perspective view of a key and a keyway of the apparatus in FIG. 1.
Figure 6:
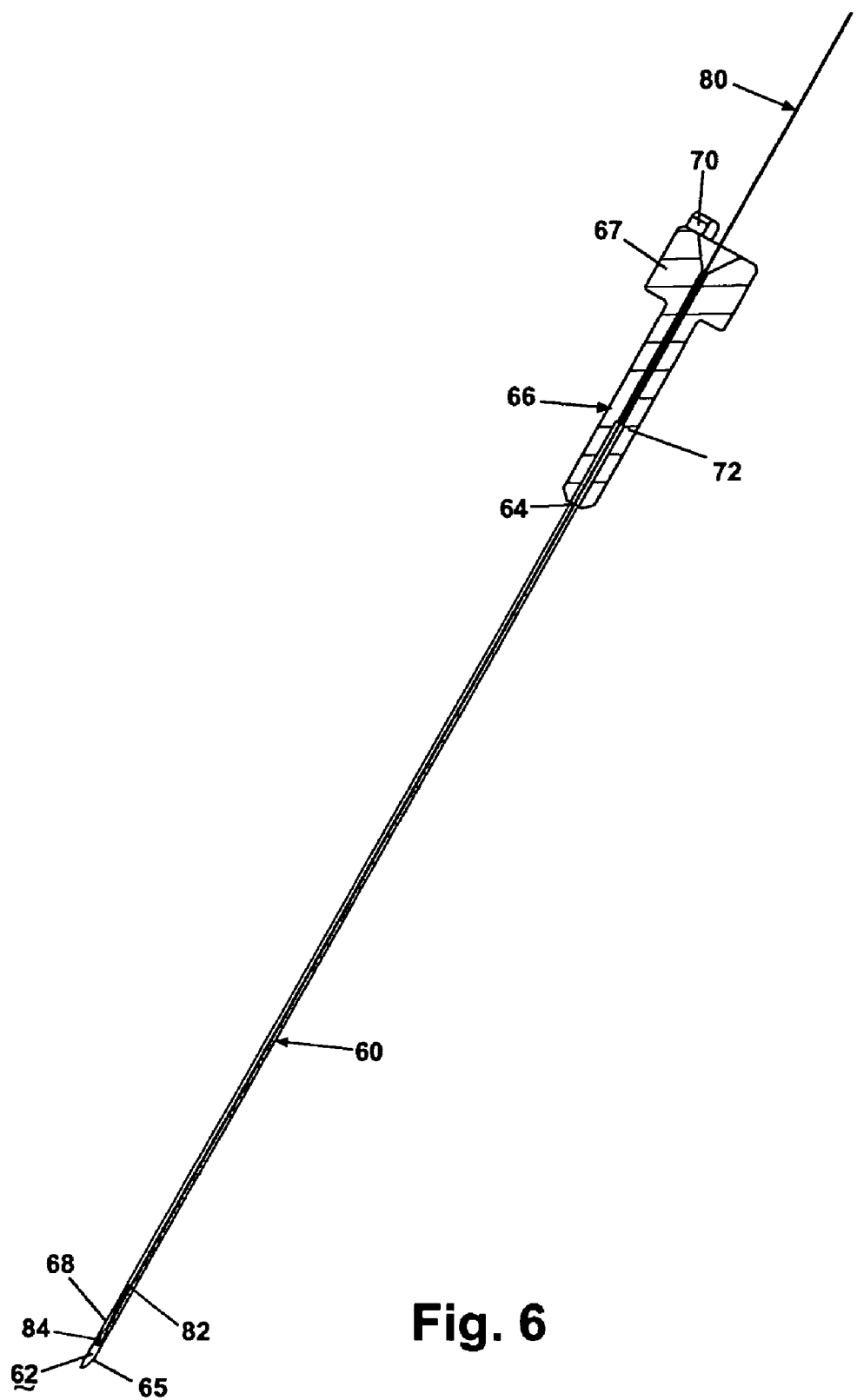
FIG. 6 is an enlarged sectional view of the cannula and the key of the apparatus in FIG. 1 and showing the preloaded localization wire disposed therein.

Referring now to FIGS. 4 and 6, the cannula 60 defines a lumen 62 and comprises a proximal end 64 mounted to a key 66 and a distal end 68 that forms an insertion tip 65. The key 66 includes a collar 67 with diametrically opposed key projections 70 and a sheath 72 that extends distally from the collar 67 to encase the proximal end 64 of the cannula 60. The distal end 68 of the cannula 60 can be sharpened to facilitate insertion into the tissue mass 150 (FIG. 7). Further, cannula 60 comprises an imageable portion 74, preferably at least at the distal end 68, for enhanced visibility using common imaging techniques, such as radiography, ultrasonography, and magnetic resonance imaging (MRI). Multiple imageable portions 74 can be spaced along the cannula 60 at predetermined intervals and effectively utilized as a ruler when disposed within the tissue mass 150. Suitable cannula tips are disclosed in U.S. Pat. No. 5,490,521, issued Feb. 13, 1996 to R. E. Davis and G. L. McLellan, which is incorporated by reference. Ultrasound enhancement technology is also disclosed in U.S. Pat. No. 4,401,124, issued Aug. 30, 1983 to J. F. Guess et al.; and U.S. Pat. No. 4,582,061, issued Apr. 15, 1986 to F. J. Fry.

Figure 9:
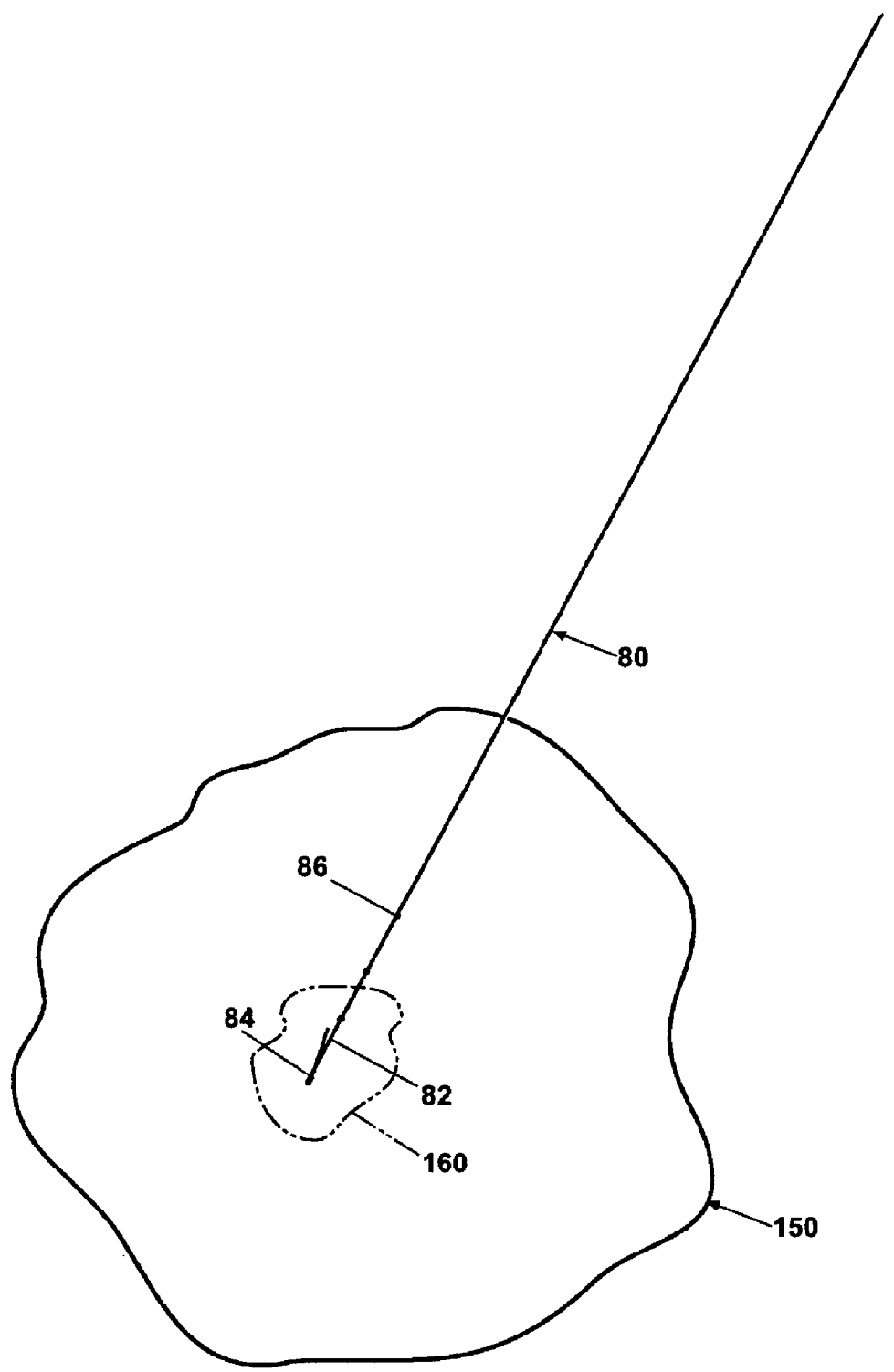
FIG. 9 is a plan view of the localization wire in FIG. 8 implanted in the tissue mass, wherein the apparatus has been removed from the localization wire.
Figure 10:
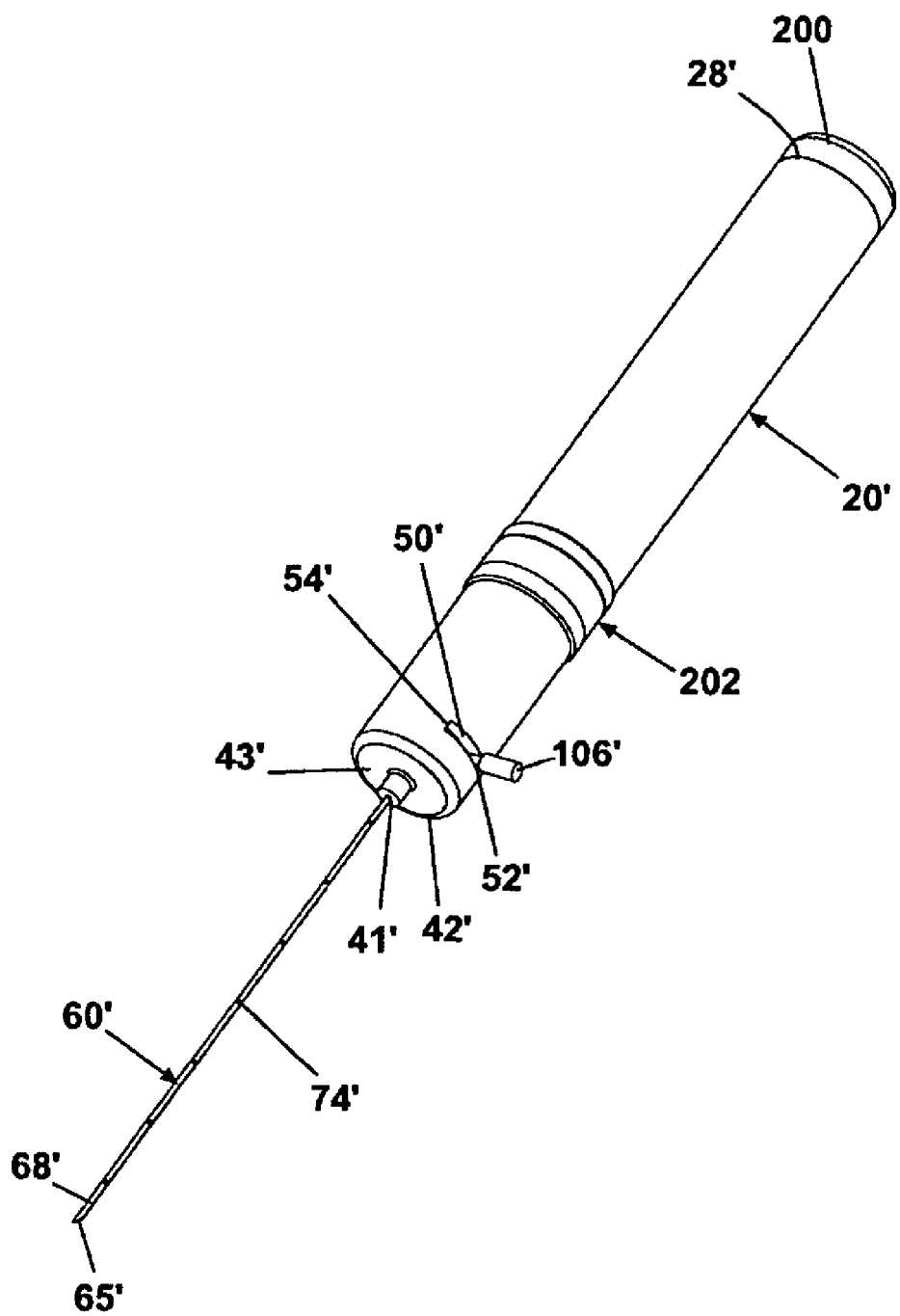
FIG. 10 is a perspective view of a second embodiment of an apparatus for implanting a preloaded localization wire according to the invention, with the apparatus shown in a cocked condition.
Figure 11:
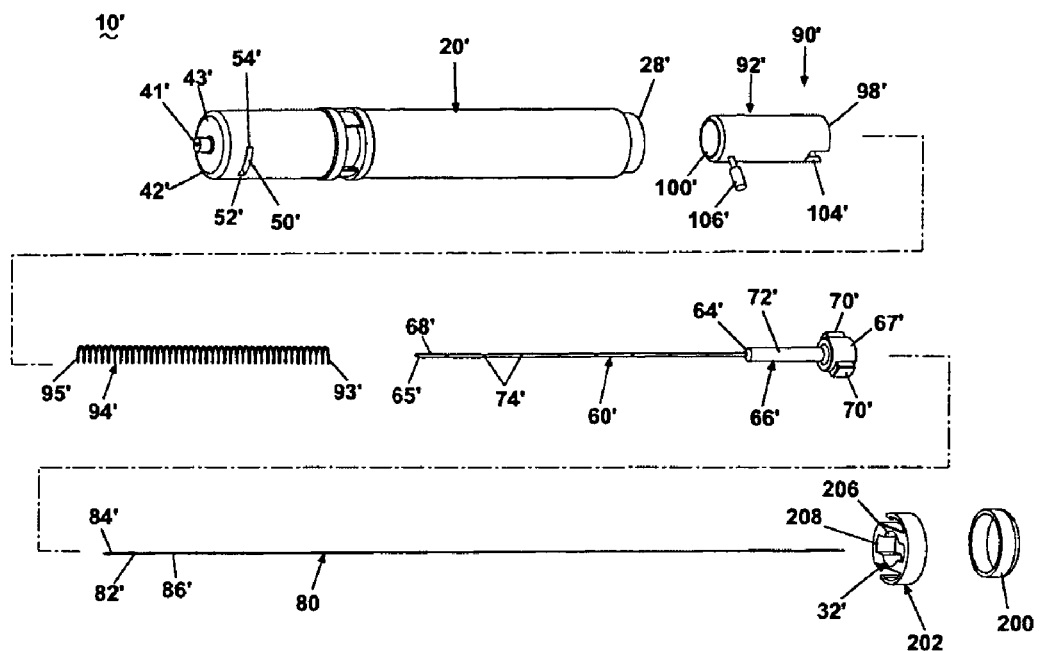
FIG. 11 is an exploded view of the apparatus in FIG. 10.
Figures 12, 12A:
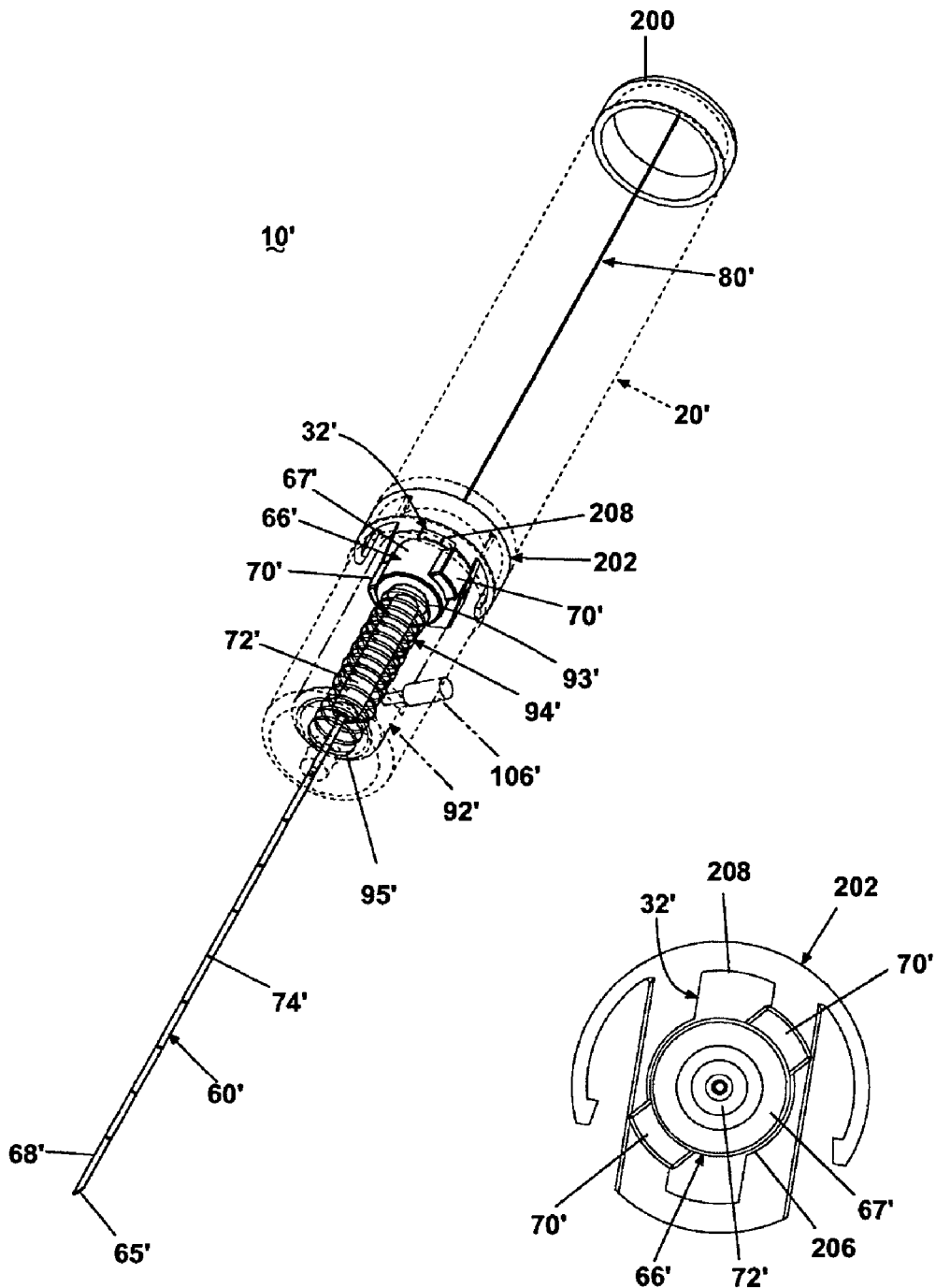
FIG. 12 is a perspective view identical to FIG. 10, wherein a handle is illustrated in phantom to show a spring-loaded cannula disposed inside the handle and the cannula is in an insertion position.
FIG. 12A is a front plan view of a key and a keyway of the apparatus in FIG. 9, wherein the key and keyway are unaligned.

With particular reference to FIGS. 4, 6 and 9, the localization wire 80 comprises a distal end 82 near which is located at least one anchor 84 for securing the localization wire 80 in the tissue mass 150. The anchor 84 in this embodiment is an integrally formed, single barb; however, the anchor 84 can be in the form of a hook, a loop, a coil, a pair of opposing barbs, or any other suitable form. Similar to the cannula 60, the localization wire 80 can comprise an imageable portion 86, at the distal end 82 or along the entire length of the wire 80, for enhanced visibility using common imaging techniques, such as radiography, ultrasonography, and magnetic resonance imaging (MRI). For example, the surface contour of the localization wire 80 can change at certain locations or at periodic intervals, such that those locations appear different from the rest of the wire 80 when using an imaging technique. The change in contour can be achieved by etching to remove material from the surface. Another example of an imageable portion 86 is incorporation of beads or loops into the wire 80 at the distal end 82 or along the entire length of the wire 80 to provide a palpable reference.

Figures 8, 8A:
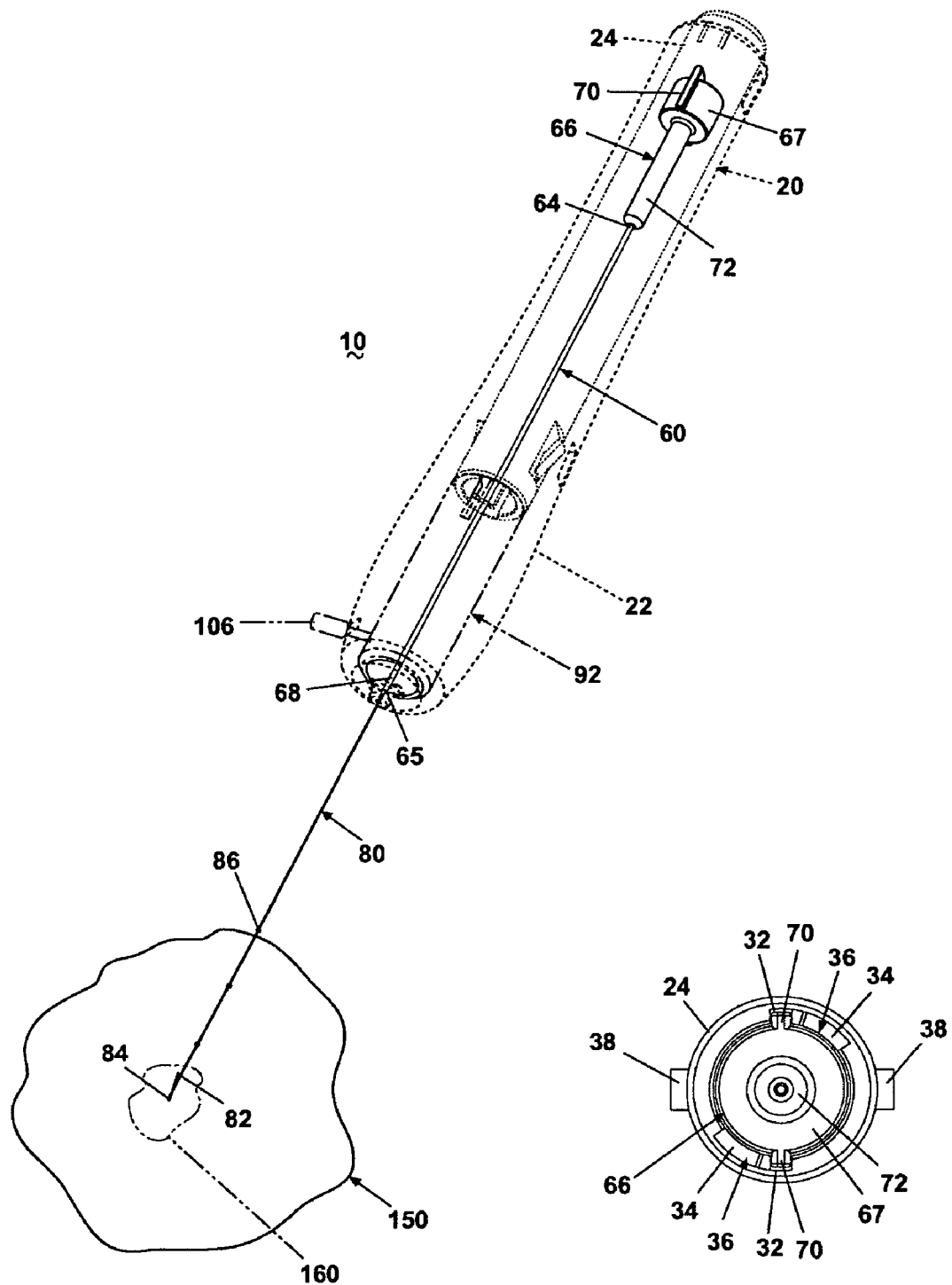
FIG. 8 is a perspective view of the apparatus in FIG. 1, wherein the cannula is in an implant position to expose the localization wire to the predetermined location of the tissue mass.
FIG. 8A is a front plan view of the key and keyway of the apparatus in FIG. 8, wherein the key and keyway are aligned.

The cannula 60 is movable between an insertion position, as illustrated in FIG. 1-3 and 7, and an implant position, as depicted in FIG. 8. In the insertion position, the cannula 60 extends distally from the handle 20 to facilitate insertion into the tissue mass 150, and the anchor 84 is preferably completely contained within the cannula 60. In this embodiment, the key 66 abuts the distal end 30 of the handle base portion 24, and the key projections 70 are seated in the circumferential recesses 34 of the grooves 36 but are spaced from the respective longitudinal keyways 32. The configuration of the key 66 relative to the grooves 36 when the cannula 60 is in the insertion position is best viewed in FIG. 7A. In the implant position, the cannula is proximally retracted into the hollow interior 26 of the handle 20, and the anchor 84 is located exteriorly of the cannula 60 and exposed to the tissue mass 150. In this embodiment, the key projections 70 are rotated relative to the insertion position such that they are aligned with the respective longitudinal keyways 32 to enable displacement of the key 66 and, therefore, the cannula 60 into the handle grip portion 24. The position of the key projections 70 relative to the grooves 36 when the cannula 60 is in the implant position is best seen in FIG. 8A.

The localization wire 80 and the cannula 60 are sized such that they are independently moveable. In other words, movement of the cannula 60 does not induce movement of the localization wire 80, and the localization wire 80 is free to move within and relative to the cannula 60. As a result, the localization wire 80 is stationary during retraction of the cannula 60, and inadvertent displacement of the localization wire 80 is avoided.

To ensure that the localization wire 80 does not move in response to the movement of the cannula 60, the localization wire 80 can have a portion that is fixed relative to the handle or some other structure that does not move with the cannula 60.

When the cannula 60 is in the insertion position, the localization wire 80 is preloaded within the lumen 62 and extends into the hollow interior 26 of the handle base portion 24, as seen in FIG. 3. In particular, the distal end 82 of the localization wire 80 is positioned near the insertion tip 65 such that the cannula 60 sheaths the anchor 84, as shown in FIG. 6. If necessary, the anchor 84 can be compressed to fit within the lumen 62. When the cannula 60 retracts to the implant position, the localization wire 80 is stationary; therefore, the distal end 82 and anchor 84 of the localization wire 80 become exposed to their surroundings, as illustrated in FIG. 8. Because the anchor 84 of the localization wire 80 is disposed near the cannula insertion tip 65 and is not displaced during retraction of the cannula 60, the practitioner only has to position the insertion tip 65 when the cannula 60 is inserted into tissue mass 150.

The actuator 90 for automatically moving the cannula 60 from the insertion position to the implant position comprises a biasing element, which is shown as a spring 94 with a proximal end 93 and distal end 95, and a trigger 92 in operable communication with the key 66. The trigger 92 includes a hollow finger 96, which has open proximal and distal ends 98 and 100, rotatably disposed in the grip portion 22. Diametrically opposed longitudinal grooves 104 sized to receive the diametrically opposed key projections 70 extend from the proximal end 98 of the finger 96. The spring 94 extends through the hollow finger 96, with the proximal and distal ends 93 and 95 of the spring 94 abutting the key collar 67 and the wall 43 of the grip portion 22, respectively.

The trigger 92 further comprises a trigger arm 106 that extends radially from the finger 96 and through the transverse slot 50 in the grip portion 22. Movement of the trigger arm 106 within the transverse slot 50 rotates the trigger 92 between a ready position and a release position. When the trigger arm 106 is adjacent the first trigger arm stop 52 (FIG. 7), the trigger 92 is in the ready position. Movement of the trigger arm 106 to the second trigger arm stop 54 (FIG. 8) places the trigger 92 in the release position.

The actuator 90 is operable between a charged condition and a discharged condition. When the actuator 90 is in the charged condition, as in FIG. 7, the trigger 92 is in the ready position, and the spring 94 is in a compressed state. Additionally, the finger grooves 104 engage the key projections 70, which are unaligned with the respective longitudinal keyways 32. When the actuator 90 is in the discharged condition, as in FIG. 8, the trigger 92 is in the release position, and the spring 94 is in an expanded state. To move the actuator 90 from the charged condition to the discharged condition, the trigger arm 106 is circumferentially displaced along the transverse slot 50 to effect rotation of the finger 96 and to move the trigger 92 to the release position. Because the finger grooves 104 are engaged with the key projections 70, the key 66 rotates with the finger 96 until the key projections 70 align with the longitudinal keyways 32. Once the key projections 70 and the longitudinal keyways 32 are aligned, the spring 94 expands from the compressed state and pushes the cannula 60 to the implant position. In FIG. 8, the spring 94 is not shown in order to provide a clear illustration of the interior of the implanting apparatus 10.

Referring again to FIG. 2, in operation, the apparatus 10 begins with the handle 20 in the uncocked condition and the cannula 60 in the insertion position. In this position, the cannula 60 and localization wire 80 are protected by the handle 20 from being bent or damaged during handling prior to implanting the localization wire 80. Even though the trigger 92 is in the ready position, the spring 94 in the expanded state, and the finger grooves 104 are not engaged with the key projections 70; therefore, the actuator 90 is not yet in the charged condition. Consequently, accidental discharge of the actuator 90 when the apparatus 10 is in the uncocked condition is not possible.

To move the handle 20 to the cocked condition in FIG. 7, a practitioner situates the proximal end 28 of the body portion 24 against a surface and applies a proximal force to the grip portion to slide the grip portion 22 over the body portion 24. Alternatively, the body portion 24 can be pushed distally into the grip portion 22. Movement of the handle 20 from the uncocked condition to the cocked condition exposes the cannula 60 and sets the actuator 90 in the charged condition. In particular, movement of the grip portion 22 displaces the actuator finger 96 towards the body portion 24 and transforms the spring 94 from the expanded state to the compressed state. As the finger 96 approaches the key 66, the finger grooves 104 engage the key projections 70. The cannula 60 with the localization wire 80 therein remains in the insertion position.

With the apparatus 10 in the condition shown in FIG. 7, the cannula 60 is inserted into the tissue mass 150 so that its insertion tip 65 is at the predetermined location, which is illustrated as a lesion 160 in FIGS. 7 and 8. Preferably, the cannula 60 with the localization wire 80 contained therein is positioned within the tissue mass 150 by using the imageable portions 74 in conjunction with a suitable imaging system. As stated above, only the cannula insertion tip 65 requires positioning when the cannula 60 is inserted into the tissue mass 150. The design of the apparatus 10 enables the practitioner to use one hand to move the handle 20 to the cocked condition and insert the cannula 60 into the tissue mass 150; the other hand can hold an ultrasonic transducer to aid in positioning the cannula 60 and the localization wire 80.

Referring now to FIG. 8, to implant the localization wire 80, the practitioner, preferably using the same hand as above for cocking and inserting the apparatus 10, moves the actuator 90 to the discharged condition by rotating the trigger arm 106 from the first trigger arm stop 52 to the second trigger arm stop 54 to move the trigger 92 from the ready position to the release position. As discussed earlier, rotation of the trigger arm 106 induces rotation of the finger 96 and the key 66. Upon sufficient rotation of the key 66, the key projections 70 align with the longitudinal keyways 32, thereby enabling proximal displacement of the cannula 60. Once alignment is achieved, the spring 94 simultaneously expands from the compressed state and forces the cannula 60 to the implant position. The cannula 60 retracts relative to the stationary localization wire 80 and into the handle 20. Preferably, the retracted cannula 60, including the insertion tip 65, is contained entirely within the handle 20 for safety purposes. Retraction of the cannula 60 exposes the distal end 82 of the localization wire 80 to the tissue mass 150, and the anchor 84 deploys at the predetermined location to embed the localization wire 80 in the tissue mass 150. Advantageously, the localization wire 80 does not move during the implant process, and, consequently, the anchor 84 is embedded where the practitioner positions it during insertion, which greatly improves the placement accuracy over the prior art. After the anchor 84 is implanted at the predetermined location, the apparatus 10 is removed from the localization wire 80, which remains in the tissue mass 150, as depicted in FIG. 9.

A second embodiment of an implanting apparatus 10' according to the invention is illustrated in FIGS. 10-13A where similar components are identified with the same reference numeral bearing a prime (') symbol. The second embodiment is very similar to the first embodiment; the primary difference is the handle 20' of the second embodiment. The first embodiment handle 20 comprises the grip portion 22 and the body portion 24, which are initially in an uncocked condition. Conversely, the second embodiment handle 20' is a single element having a cap 200 at its proximal end 28' and a distal wall 43' with an aperture 41' for slidably receiving the cannula 60'. The handle 20' does not have a similar uncocked condition; rather, the second embodiment is assembled and shipped in the cocked condition, with the cannula being exposed to the surrounding environment.

Figures 13, 13A:
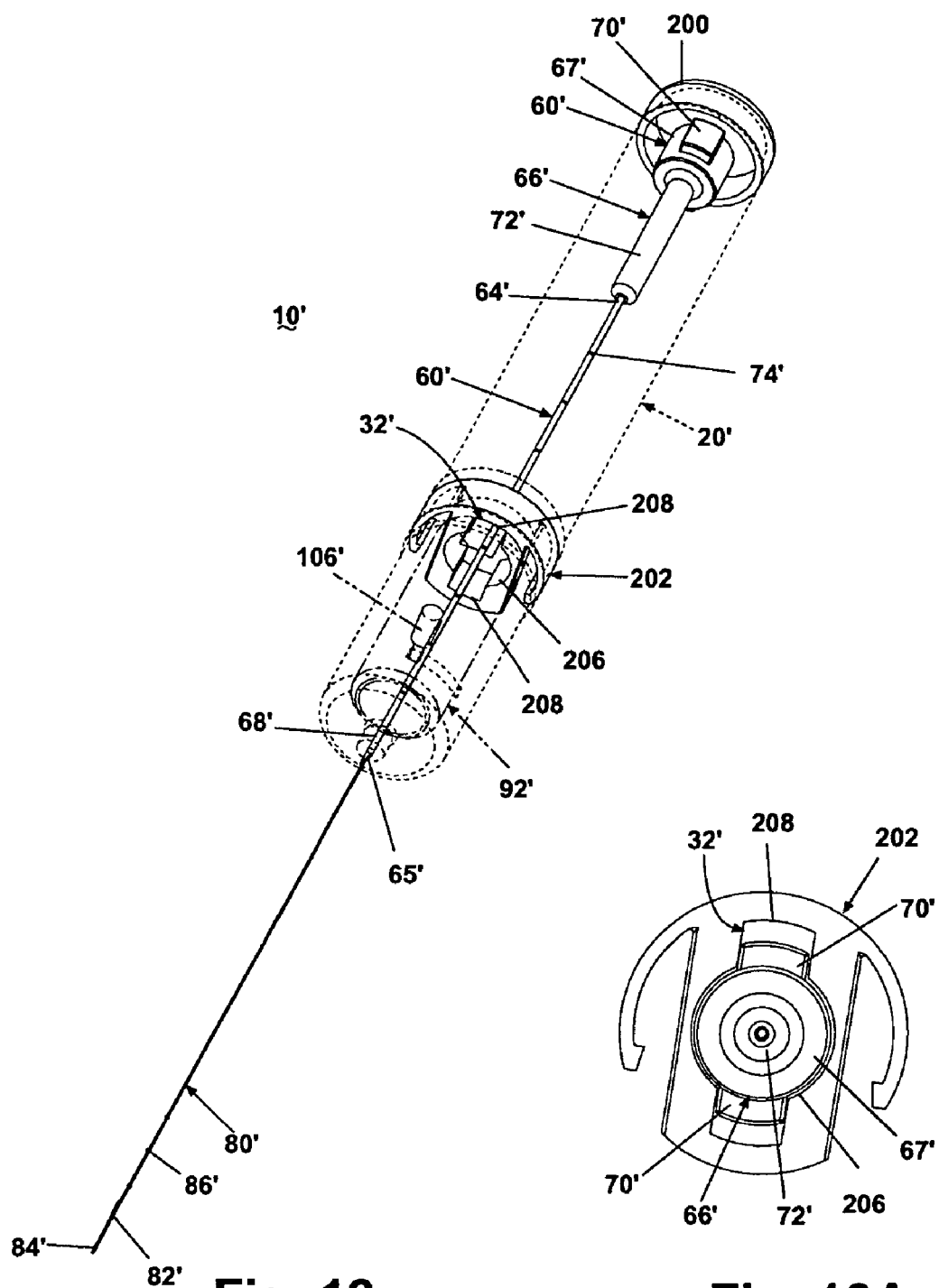
FIG. 13 is a perspective view of the apparatus in FIG. 10, wherein the cannula is in an implant position to expose the localization wire.
FIG. 13A is a front plan view of the key and the keyway of the apparatus in FIG. 13, wherein the key and keyway are aligned.
Figure 14:
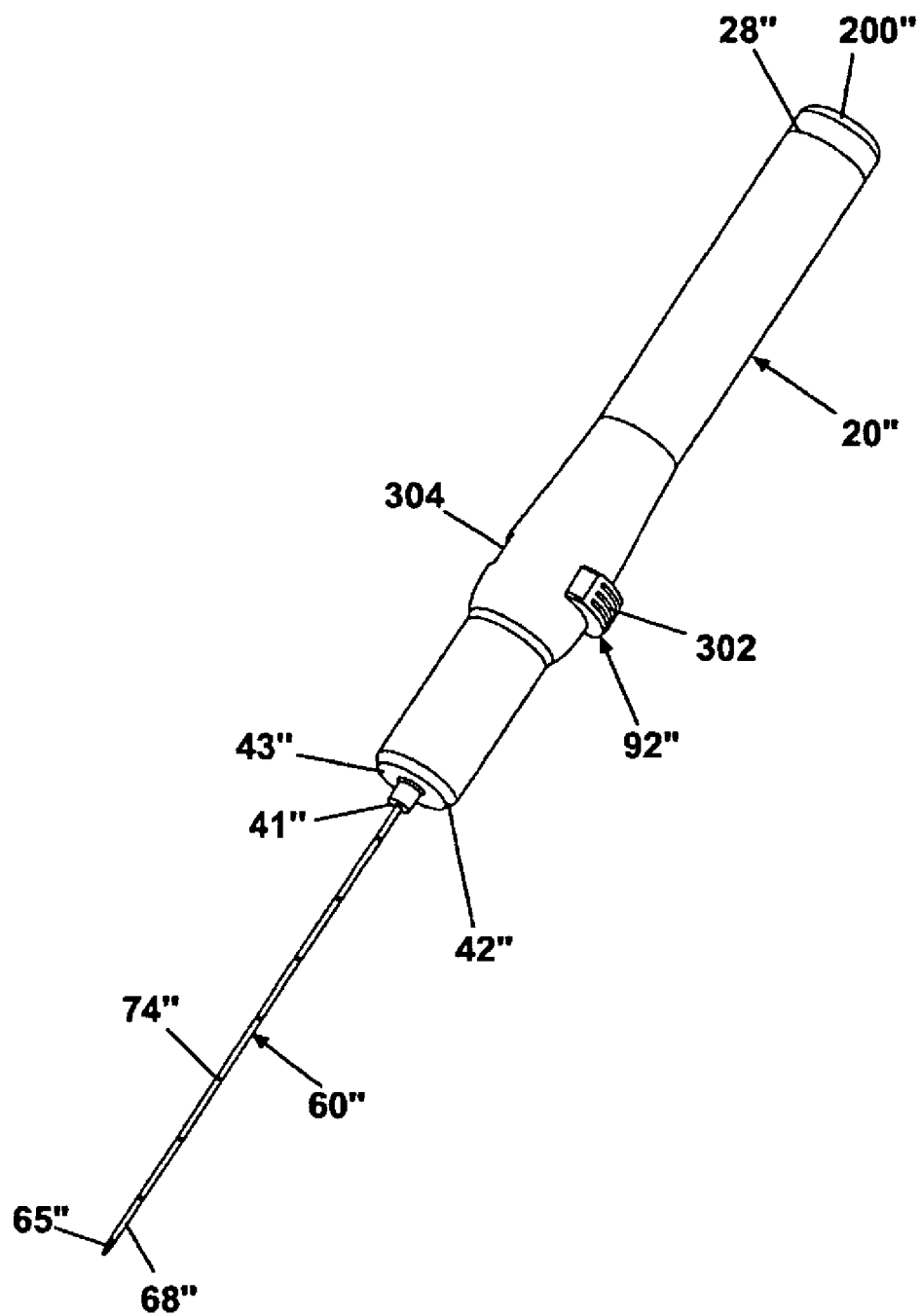
FIG. 14 is a perspective view of a third embodiment of an apparatus for implanting a preloaded localization wire according to the invention, with the apparatus shown in a cocked condition.

Referring to FIGS. 11-13A, instead of grooves 36 on the inside surface of the handle 20, the second embodiment handle 20' comprises a keyway disk 202 disposed adjacent to the proximal end 98' of the trigger finger 96'. The keyway disk 202 includes a keyway 32' having a shape corresponding to that of the key collar 67' and the key projections 70'. In the illustrated embodiment, the keyway 32' comprises a circular portion 206 and diametrically opposed rectangular portions 208. When the cannula 60' is in the insertion position in FIG. 12, the anchor 84' of the localization wire 80' is retained within the cannula 60', and the key 66' abuts the distal side of the keyway disk 202 and is oriented such that the key projections 70' are not aligned with the rectangular portions 208. This configuration, best viewed in FIG. 12A, prevents movement of the cannula 60' through the keyway 32'. When the cannula 60' is in the implant position shown in FIG. 13, the key projections 70' are rotated relative to the insertion position such that they are aligned with rectangular portions 208 of the keyway 32' to enable displacement of the key 66' and, therefore, the cannula 60' into the hollow interior 26' of the handle 20', and the anchor 84' of the localization wire 80' is exterior of the cannula 60' and exposed to the surrounding tissue. In FIG. 13, the spring 94' is not shown in order to provide a clear illustration the interior of the apparatus 10'. The position of the key projections 70' relative to the keyway 32' when the cannula 60' is in the implant position is best seen in FIG. 13A.

The operation of the second embodiment is substantially the same as, if not identical to, the operation of the first embodiment, excluding the cocking step. Because the second embodiment apparatus 10' is initially in a cocked condition, the operation begins with the step of inserting the cannula 60' into the tissue mass 150'. Once the cannula 60' and the localization wire 80' are at the predetermined location, the practitioner rotates the trigger arm 106' within the transverse slot 50' to move the trigger 92' from the ready position to the release position and thereby align the key projections 70' with the longitudinal keyways 32'. Upon alignment, the spring 94' expands and forces the cannula 60' to the implant position to expose the distal end 82' of the localization wire 80' to the tissue mass 150'. After the anchor 84' is secured in the tissue mass 150', the apparatus 10' is removed from the localization wire 80'.

Figure 15:
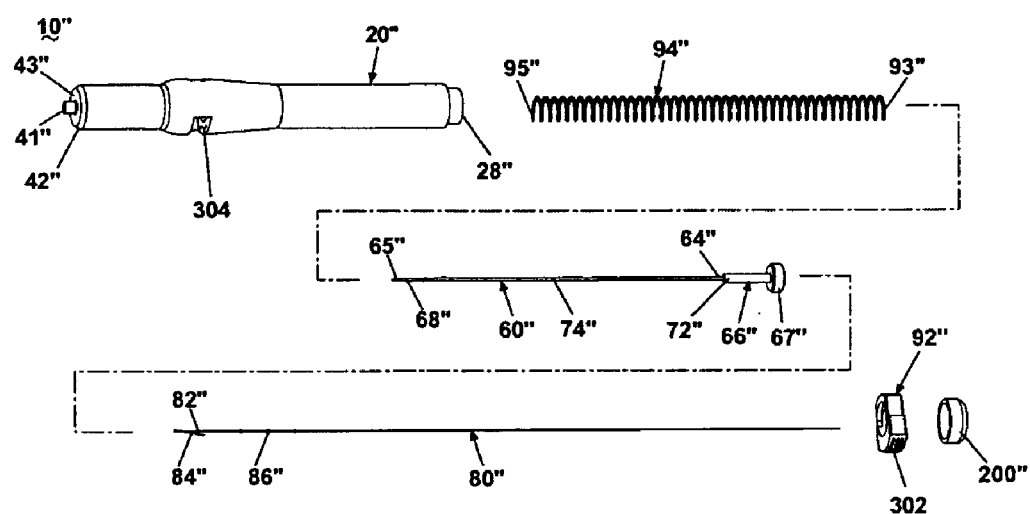
FIG. 15 is an exploded view of the apparatus in FIG. 14.
Figure 15A:
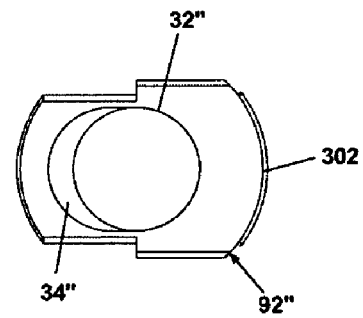
FIG. 15A is a front plan view of a trigger with a keyway from the apparatus in FIG. 15.

A third embodiment of an implanting apparatus 10" according to the invention is illustrated in FIGS. 14-17A where similar components are identified with the same reference numeral bearing a double prime (") symbol. The primary difference between the second and third embodiments is the actuator trigger 92". The third embodiment trigger 92", which is best seen in FIG. 15A, comprises a keyway 32" corresponding to the shape of the key 66", a recess 34" offset from the keyway 32", and a surface 302 designed to support a finger of the practitioner. The trigger 92" is mounted to a transverse slot 304 in the handle 20" and is slidably movable between the ready and release positions. The trigger 92" of the third embodiment effectively replaces the keyway disk 202 of the second embodiment.

Figures 16, 16A:
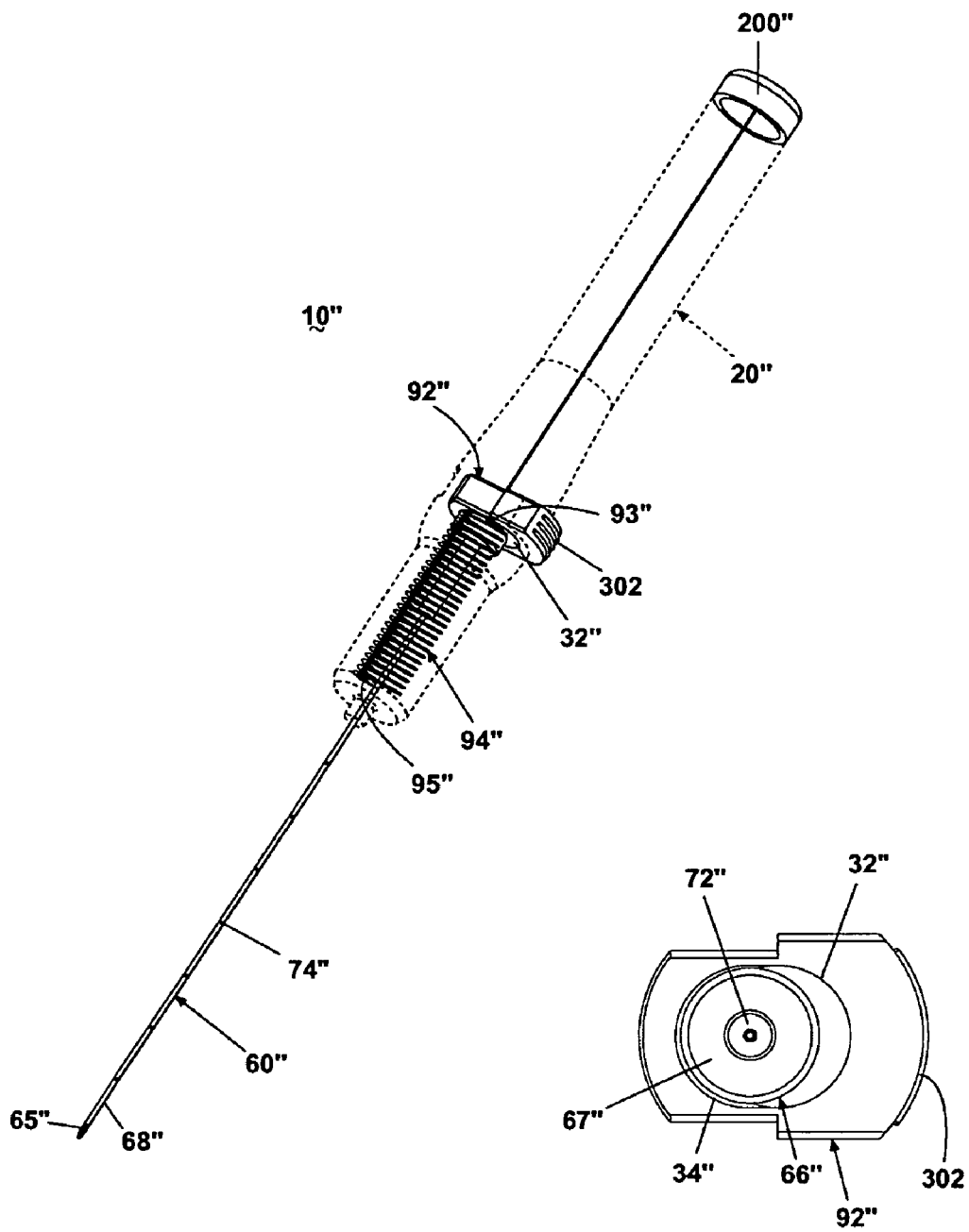
FIG. 16 is perspective view identical to FIG. 14, wherein a handle is illustrated in phantom to show a spring-loaded cannula disposed inside the handle and the cannula is in an insertion position.
FIG. 16A is a front plan view of a key and the trigger of the apparatus in FIG. 16, wherein the key and keyway are unaligned.
Figure 17:
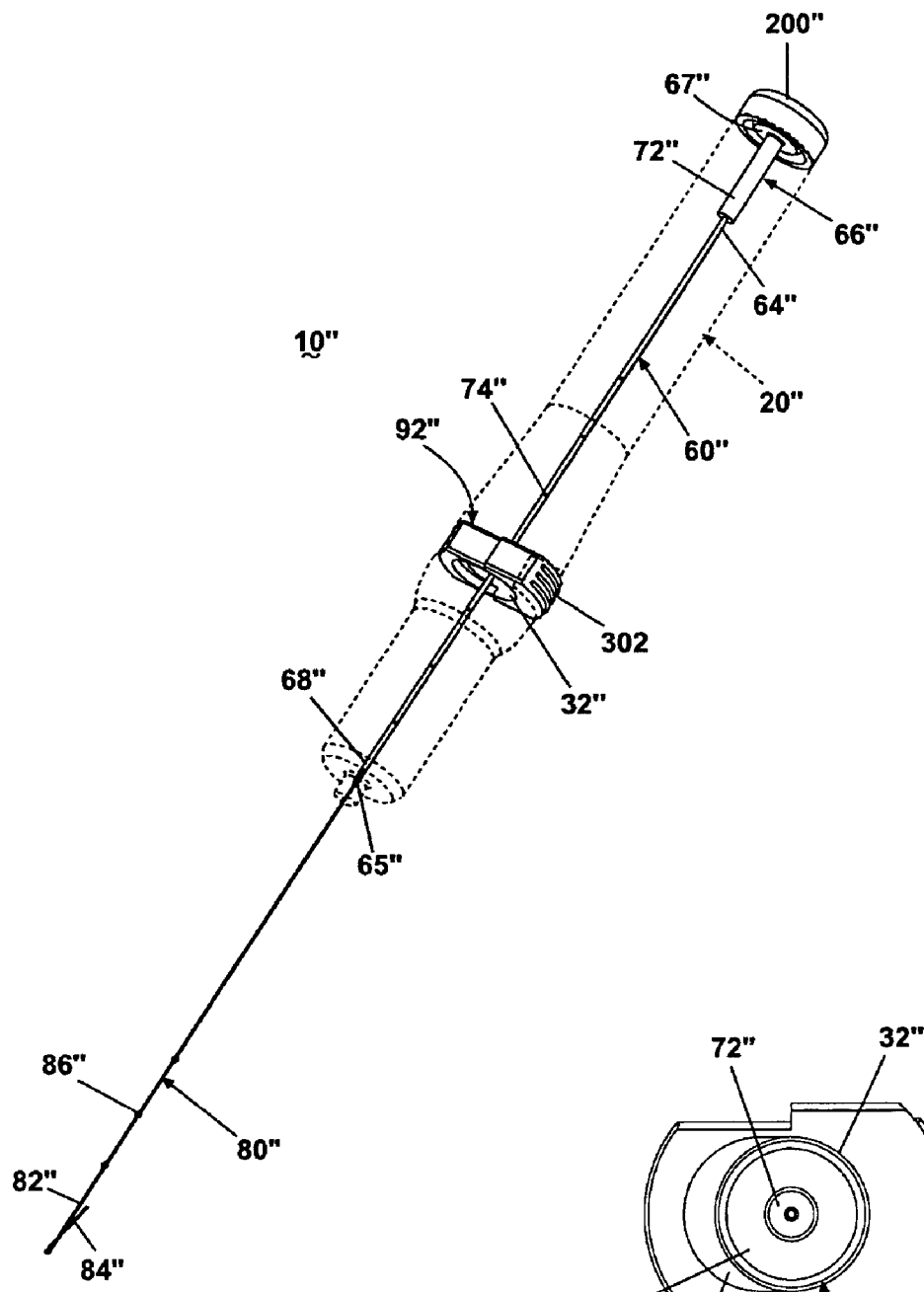
FIG. 17 is a perspective view of the apparatus in FIG. 14, wherein the cannula is in an implant position to expose the localization wire.
Figure 17A:
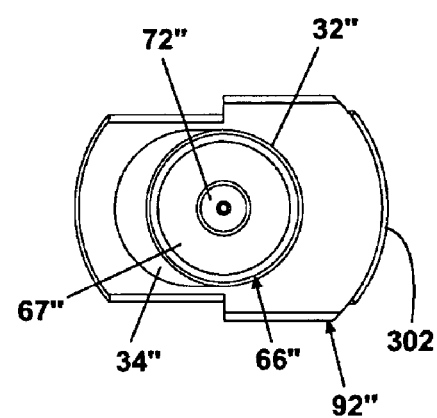
FIG. 17A is a front plan view of the key and the trigger of the apparatus in FIG. 17, wherein the key and keyway are aligned.

When the cannula 60" is in the insertion position shown in FIG. 16, the key collar 67" abuts the distal side of the trigger 92" and resides in the recess 34" such that the collar 67" is unaligned with the keyway 32". This configuration, best viewed in FIG. 16A, corresponds to the ready position of the trigger 92". In the ready position, the trigger 92" prevents retraction of the cannula 60" relative to the localization wire 80". To move the cannula 60" to the implant position shown in FIG. 17, the trigger 92" slides to the release position, wherein the keyway 32" aligns with the key collar 67" to enable displacement of the key 66" and, therefore, the cannula 60" into the hollow interior 26" of the handle 20". In FIG. 17, the spring 94" is not shown in order to provide a clear illustration the interior of the apparatus 10". The position of the key projections 70" relative to the keyway 32" when the trigger 92" is in the release position is best seen in FIG. 17A.

The operation of the third embodiment is substantially the same as the operation of the second embodiment; the primary difference is the operation of the actuator 90", particularly the trigger 92". Rather than rotating the trigger arm 106' through the transverse slot 50', the trigger 92" is actuated by pushing on the surface 302 to slide the trigger 92" through the transverse slot 304 from the ready position to the release position.

Figure 18:
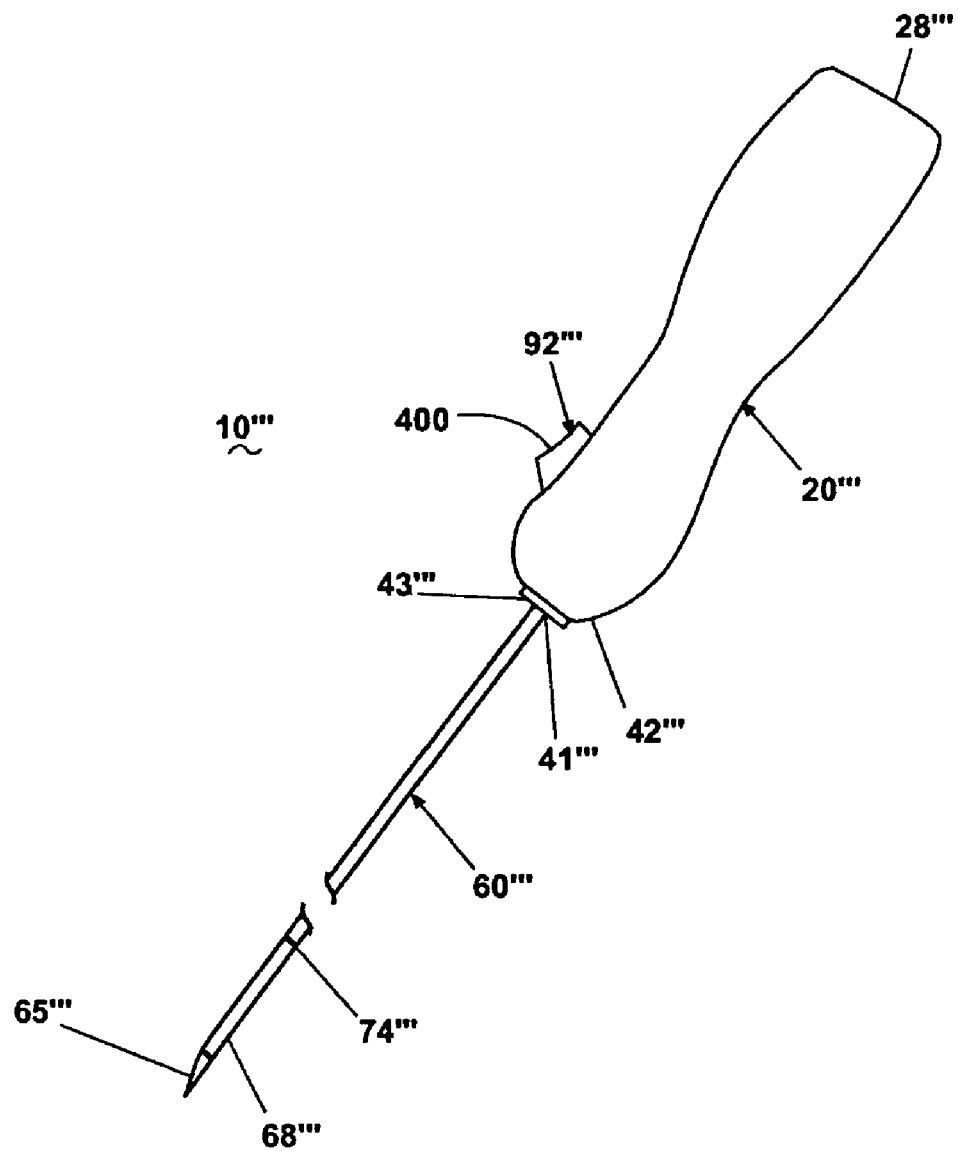
FIG. 18 is a plan view of a fourth embodiment of an apparatus for implanting a preloaded localization wire according to the invention, with the apparatus shown in a cocked condition.
Figure 19:
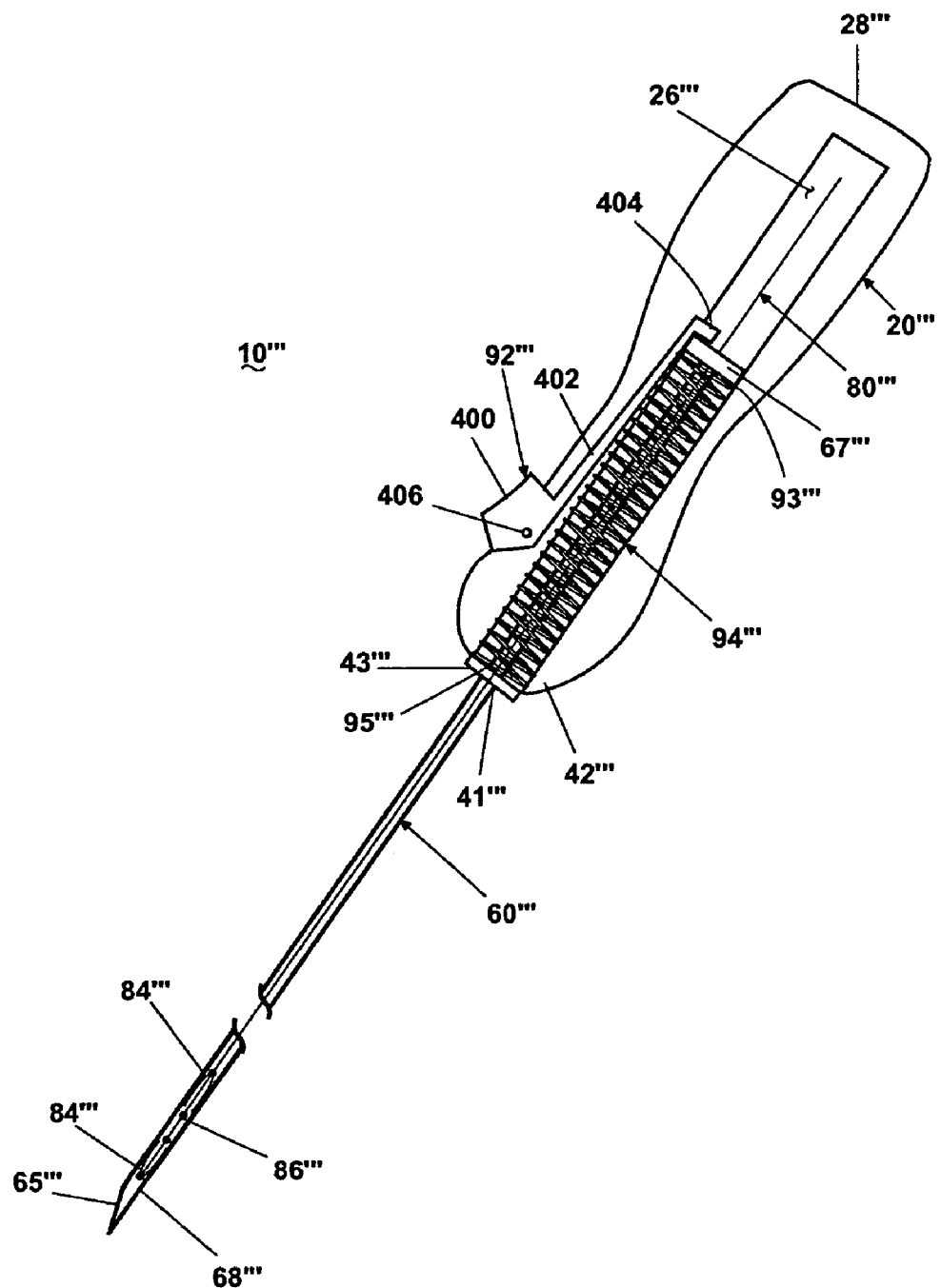
FIG. 19 is a sectional view of the apparatus in FIG. 18, wherein the cannula is in an insertion position.
Figure 20:
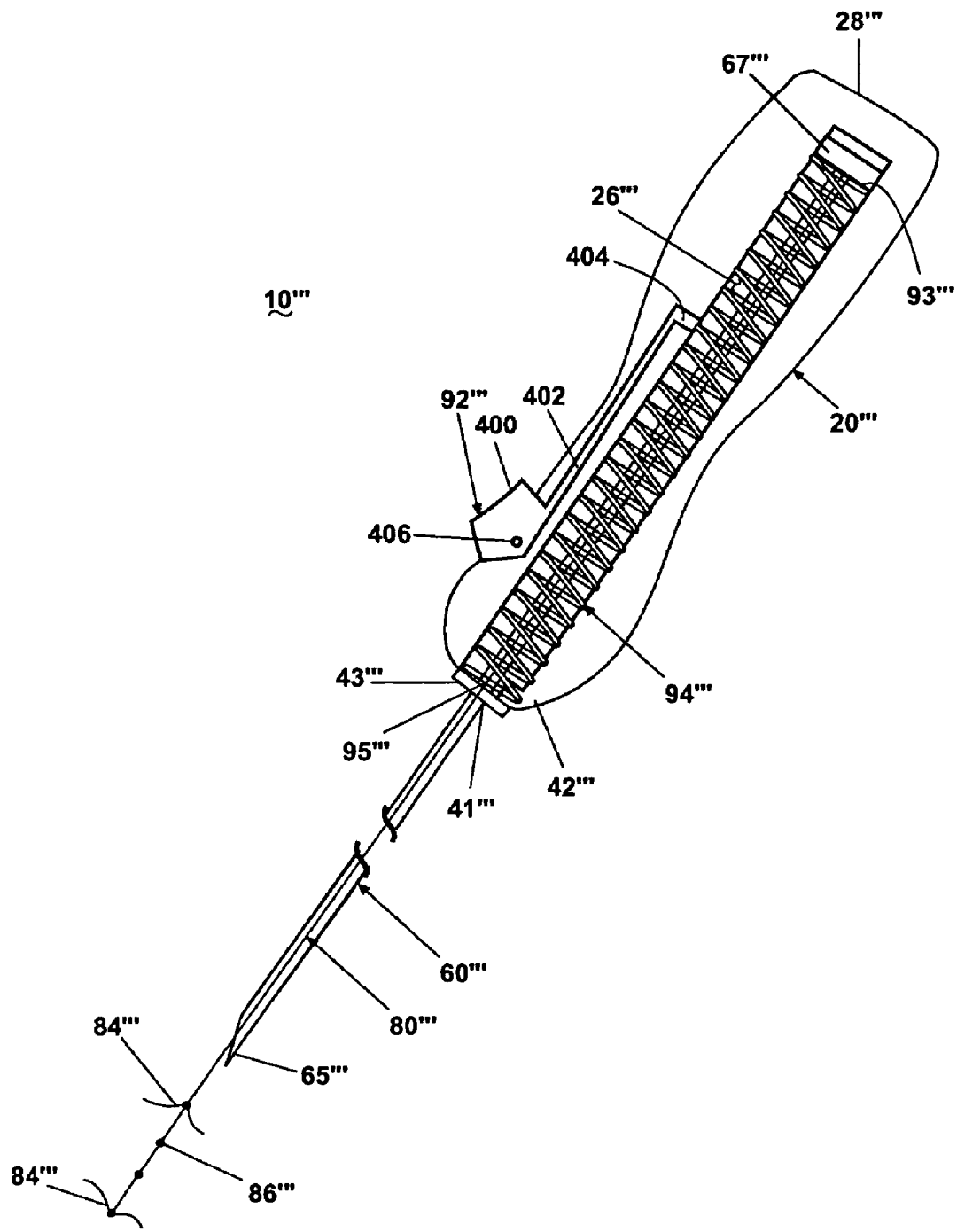
FIG. 20 is a sectional view of the apparatus in FIG. 18, wherein the cannula is in an implant position to expose the localization wire.

A fourth embodiment of a implanting apparatus 10''' according to the invention is illustrated in FIGS. 18-20, where similar components are identified with the same reference numeral bearing a triple prime ("') symbol. The fourth embodiment is substantially the same as the second and third embodiments, with the fourth embodiment illustrating an alternative actuator trigger 92'''. The trigger 92''' includes a surface 400 designed to support a finger of the practitioner and comprises a pivot arm 402 that terminates in a finger 404. The trigger 92''' is mounted to the handle 20''' at a pivot pin 406 and is pivotable between ready and release positions.

When the trigger 92''' is in the ready position shown in FIG. 19, the finger 404 abuts the proximal side of the collar 67''' to support the cannula 60''' against the bias of the spring 94''' and retain the cannula 60''' in the insertion position. To move the trigger 92''' to the release position, downward force applied to the surface 400 pivots the trigger 92''' about the pivot pin 406 to remove the finger 404 from abutting contact with the collar 67'''. As a result, the biasing force of the spring 94''' moves the cannula 60''' to the implant position.

The operation of the fourth embodiment is substantially the same as the operation of the second and third embodiments; the primary difference is the operation of the actuator 90''', particularly the actuation trigger 92'''. To discharge the actuator 90''', the practitioner simply applies a downward force to the surface 400 of the trigger 92'''.

In the descriptions of various embodiments of the implanting apparatus 10, the localization wire 80 has been shown as being completely disposed within the cannula 60 and the handle 20. However, it is within the scope of the invention for the localization wire 80 to extend through and beyond the proximal end 28 of the handle base portion 24. Such a configuration would facilitate implantation of a longer localization wire 80 with the same size apparatus 10.

To avoid accidental injury prior to insertion of the cannula 60 into the tissue mass 150, the apparatus 10 can optionally include a removable sheath or removable safety cap that encases the exposed portion of the cannula 60 or at least the insertion tip 65 of the cannula 60.

Figure 21:
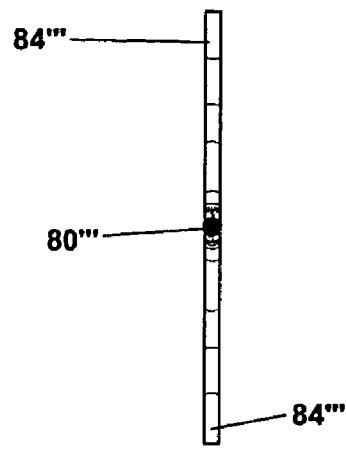
FIG. 21 is an enlarged view of the end of the localization wire of FIG. 20.

Referring to FIGS. 20 and 21, the localization wire 80''' has some unique features compared to a traditional localization wire. The localization wire 80''' comprises opposing anchors formed by opposing sets of barbs 84''' that extend from the shaft of the localization wire. The opposing sets of barbs 84''' resist the movement of the localization wire in either direction along the longitudinal axis of the shaft.

Preferably, and as illustrated, the opposing barbs are angled in opposite directions relative to the shaft. That is, each barb forms an acute interior angle relative to the shaft, but the acute interior angle faces towards an opposite end of the shaft. The opposing barb structure is ideal for use in less dense or structurally strong tissue, such as fatty tissue.

Figure 22:
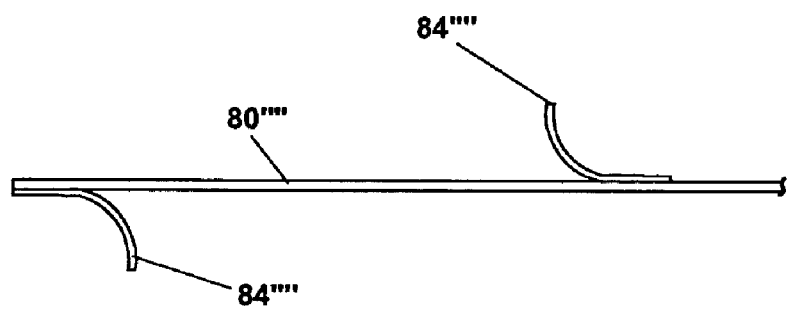
FIG. 22 is a side view of an alternative localization wire with radially offset opposing barbs.
Figure 23:
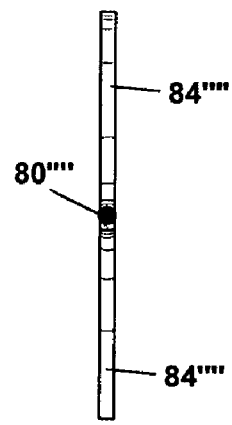
FIG. 23 is a front view of the alternative localization wire of FIG. 24.

FIGS. 22 and 23 illustrates another localization wire 80'''' incorporating the opposing barbs 84'''', which in this case are radially offset to each other and are not arranged in sets as in the localization wire 80'''.

The opposing barbs can be arranged in a variety of different ways. They can be arranged in cooperative sets, individual barbs or a combination of both. There can be an equal or unequal number of opposing barbs. The barbs can be radially aligned or unaligned.

The barbs can also be formed in a variety of ways. For example, the barbs can be integrally formed with the shaft of the localization wire, such as in bending a portion of the shaft. Alternatively, the barbs can be separate pieces affixed to the shaft, such as by laser welding separate wire elements to the shaft.

Figure 24:
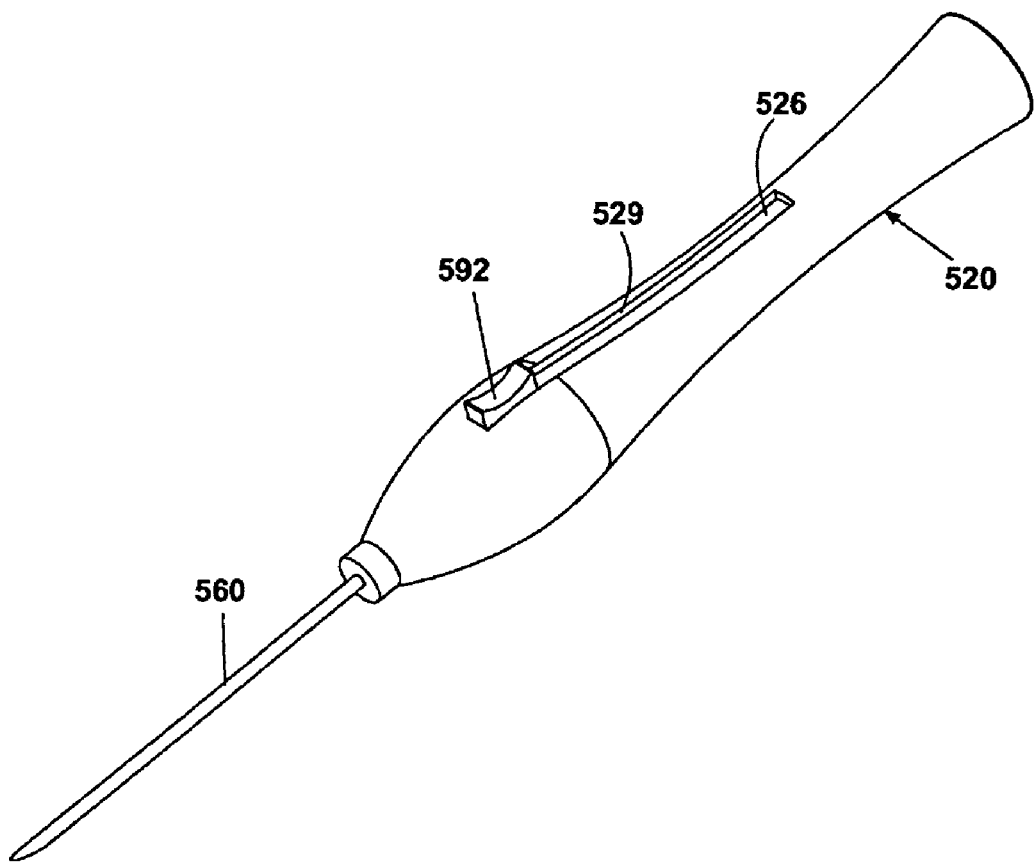
FIG. 24 is a perspective view of a fifth embodiment of an apparatus for implanting a preloaded localization wire according to the invention, with the apparatus shown in the cocked position and a cannula in the insertion position.
Figure 25:
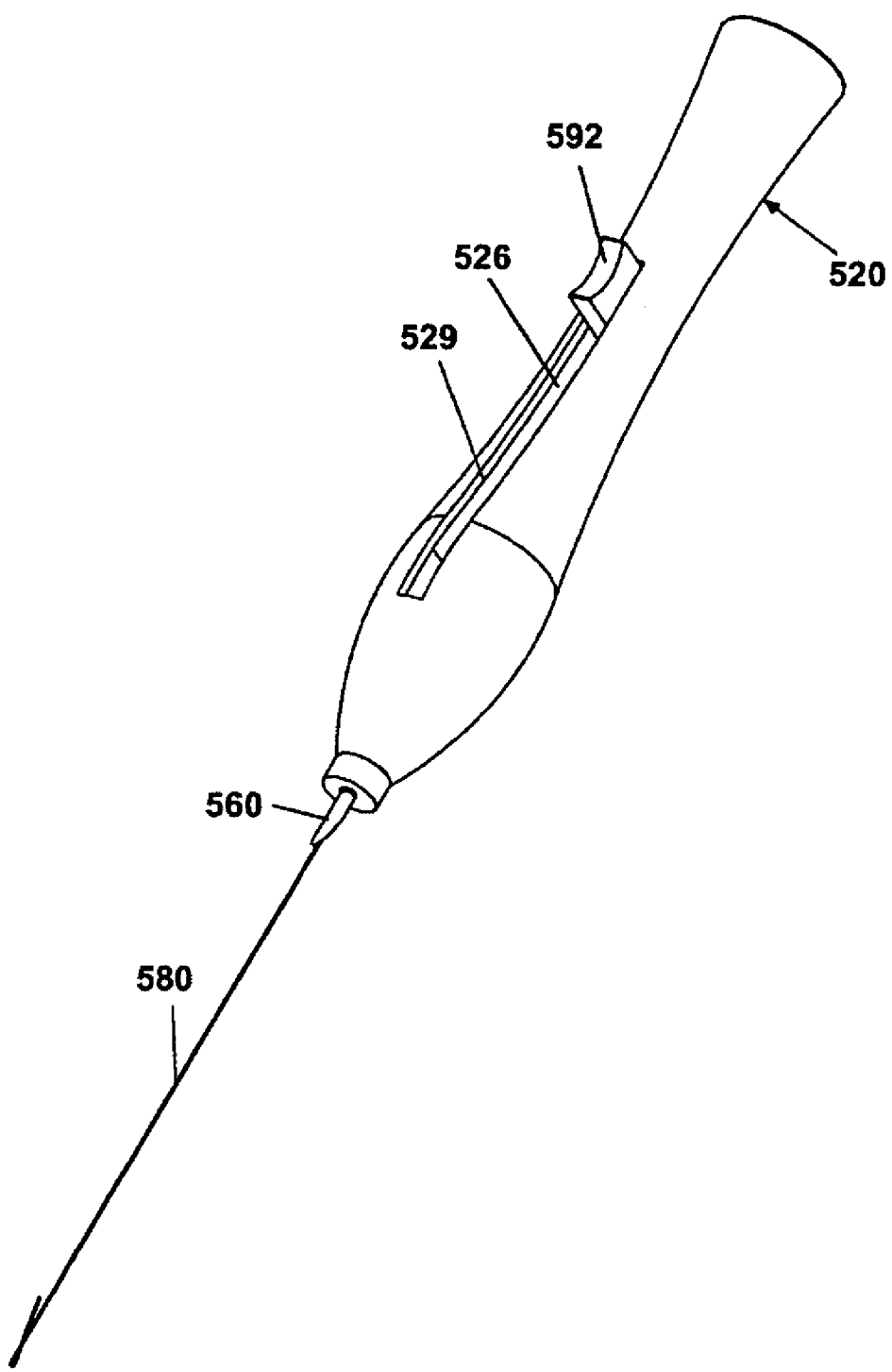
FIG. 25 is a perspective view similar to FIG. 24 except that the apparatus is shown in the uncocked position and the cannula in the implant position.
Figure 26:
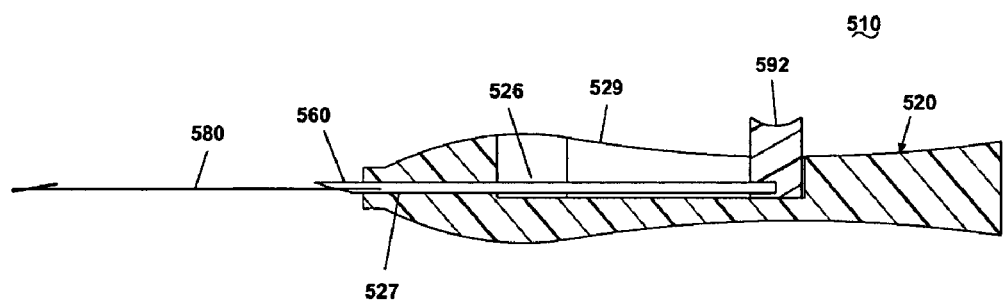
FIG. 26 is a longitudinal sectional view of the apparatus of FIG. 25.

FIGS. 24-26 illustrate a fifth embodiment apparatus 510 for implanting a localization wire. The fifth embodiment 510 comprises a handle 520, with a hollow interior 526. A passageway 527 extends from the hollow interior 526 to the nose or distal end of the handle 520. A longitudinal slot 529 is formed in the upper surface of the handle 520 and extends to the hollow interior 526.

A cannula 560 is slidably received within the passageway 527 and can reciprocate relative to the handle. A trigger 592 in the form of a slide is received within the slot 529 and is slidably moveable between the opposing ends of the slot. A proximal end of the cannula 560 is mounted to the trigger, such that the sliding movement of the trigger in the slot 529 effects the sliding movement of the cannula 560 relative to the handle 520.

A localization wire 580 is preloaded into the cannula. The sliding of the cannula into the handle results in the exposing of the localization wire to the environment previously surrounding the cannula.

In operation, the apparatus 510 is grasped by the user in the condition as illustrated in FIG. 24. In this condition, the apparatus is cocked and the cannula is in the insertion position. The user then inserts the cannula into the tissue mass, directly or through a positioning cannula, and locates the cannula as desired. The user then slides the trigger 592 to the release position as illustrated in FIG. 25, which causes the cannula to retract relative to the localization wire and expose the localization wire to the surrounding tissue. The user can then pull on the handle to withdraw the cannula from the tissue, leaving the localization wire.

The main difference between the fifth embodiment and the prior embodiments is that the cannula is manually moved from the insert position to the implant position. The prior embodiments automatically, not manually, moved the cannula. While the manual movement of the fifth embodiment is a more simple implementation, it is not preferred over the automatic implanting. It is believed that the automatic implanting is more accurate in that the user will be less like to move the apparatus relative to the tissue mass, thereby increasing the accuracy of the placement of the localization wire.

The inventive apparatus for percutaneously implanting a localization wire offers several advantages. Because the process of implanting the localization wire involves retracting the cannula without axial displacement of the localization wire, the practitioner can position the localization wire, which only requires positioning the insertion tip of the cannula, at the desired implantation location during insertion of the apparatus into the tissue mass. This feature facilitates accurate placement of the localization wire within the tissue mass, which is critical to pinpointing the predetermined location during future procedures. Retraction of the entire cannula, including the insertion tip, into to the handle prevents accidental injury during removal of the device. Additionally, the actuator of the inventive apparatus retracts the cannula automatically, thereby ensuring that a suitable force is applied to the cannula and reducing the possibility of human error. Because the inventive apparatus has a preloaded localization wire and can be operated with a single hand, the practitioner can utilize the other hand to control an imaging system and does not require the assistance of a third hand. Furthermore, the first embodiment of the apparatus is provided in an uncocked condition wherein the spring is in an expanded state, which not only prevents accidental discharge but also increases the shelf life of the spring and, therefore, the apparatus.

While the invention has been specifically described in connection with certain specific embodiments thereof, it is to be understood that this is by way of illustration and not of limitation, and the scope of the appended claims should be construed as broadly as the prior art will permit.

The invention claimed is:

1. An apparatus for percutaneously implanting a localization wire within a tissue mass, comprising:
    a handle defining a hollow interior and an end;
    a cannula defining a lumen and having a distal end forming an insertion tip, wherein the cannula is slidably mounted to the end for movement relative to the handle between an insertion position and a retracted position;
    a collar mounted to the cannula and configured to define a key;
    a localization wire positioned to extend from the handle and into the lumen of the cannula, the localization wire having a distal end that is positioned near the insertion tip and contained within the lumen when the cannula is in the insertion position, wherein the localization wire comprises at least one anchor adapted to hold the localization wire in the tissue mass, the cannula and the localization wire being configured such that each of the at least one anchor remains completely contained in the cannula when the cannula is in the insertion position prior to the cannula being moved to the retracted position;
    a keyway shaped for receiving the key;
    an actuator comprising a biasing element in operable communication with the cannula and configured such that when the key and the keyway are unaligned the biasing element is in a charged condition and when the key and the keyway are aligned the biasing element is in a discharged condition; and
    a trigger rotatably mounted to the handle and operably connected to the key such that rotation of the trigger from a ready position to a release position aligns the key with the keyway to release the biasing element from the charged condition to the discharged condition to move the cannula from the insertion position to the retracted position;
    wherein the biasing element is located within the hollow interior extending between the end and the collar to retract the cannula from the insertion position to the retracted position to expose the distal end of the localization wire to the tissue mass and expose each of the at least one anchor to the tissue mass without inducing movement of the localization wire, and with the cannula being removable from the localization wire in its entirety.

2. The apparatus of claim 1 wherein the insertion tip is sharpened to aid in the insertion of the cannula into the tissue mass.

3. The apparatus of claim 1 wherein the cannula further comprises at least one imageable portion.

4. The apparatus of claim 3 wherein the at least one imageable portion comprises multiple spaced imageable portions.

5. The apparatus of claim 1 wherein the at least one anchor comprises opposing anchors.

6. The apparatus of claim 5 wherein the opposing anchors comprise at least two opposing anchors that are radially offset.

7. The apparatus of claim 6 wherein the opposing anchors are arranged in sets.

8. The apparatus of claim 1 wherein the at least one anchor is a barb.

9. The apparatus of claim 8 wherein the barb is integrally formed with the localization wire.

10. The apparatus of claim 1 wherein the localization wire comprises an imageable portion.

11. The apparatus of claim 10 wherein the imageable portion comprises etched portions spaced at intervals along the localization wire.

12. The apparatus of claim 1 wherein the actuator is configured to automatically retract the cannula relative to the localization wire.

13. The apparatus of claim 1 wherein the biasing element is a spring in operable communication with the trigger such that movement of the trigger from the ready position to the release position releases the spring from a compressed state to an expanded state to move the cannula from the insertion position to the retracted position.

14. The apparatus of claim 1, wherein the handle comprises a base and a grip, with the grip being slidably mounted to the base for movement between a first position, where the cannula and localization wire are substantially received within the grip, and a second position, where the cannula and localization wire are substantially exteriorly of the grip.

15. The apparatus of claim 14, wherein when the grip is moved to the second position, the actuator is moved to the charged condition.

16. The apparatus of claim 15, wherein the spring is disposed between the base and the grip and the spring is compressed when the grip is moved to the second position.

17. The apparatus of claim 14, wherein the cannula has a proximal end mounted to the base.

18. The apparatus of claim 13, wherein the spring is located within the hollow interior and extends between the end and a collar extending from the cannula.

19. The apparatus of claim 13 wherein the trigger includes a finger that abuts the collar when the trigger is in the ready position, and can be rotated to the release position to remove the finger from abutting contact with the collar to release the spring.

20. The apparatus of claim 13, wherein the trigger forms the keyway and displacement of the trigger to the release position aligns the key with the keyway to thereby release the spring.

21. The apparatus of claim 1, wherein the localization wire is contained entirely within the cannula and the handle.

22. The apparatus of claim 1, wherein the handle has a base mounting a proximal end of the cannula, and a grip slidably mounted to the base for movement between a first position, where the cannula is substantially received within the grip, and a second position, where the cannula is substantially exteriorly of the grip.

23. The apparatus of claim 22 wherein when the grip is moved to the second position, the actuator is moved to the charged condition.

24. The apparatus of claim 23 wherein the actuator comprises a spring positioned within the grip and extending between the base and the grip, wherein when the grip is in the second position, the spring is in a compressed state.

25. The apparatus of claim 24 wherein when the actuator is moved to the discharged condition, the spring is released from the compressed state.

26. The apparatus of claim 1 wherein the actuator automatically effects the relative movement between the cannula and the localization wire.

27. An apparatus for percutaneously implanting a localization wire within a tissue mass, comprising:
a handle with a hollow interior and an end;
a cannula defining a lumen and having a distal end forming an insertion tip, the cannula being movable relative to the handle between an insertion position and a retracted position;
a collar that extends mounted to the cannula to define a key;
a localization wire located within the lumen and having a distal end near the insertion tip when the cannula is in the insertion position, wherein the localization wire comprises at least one anchor adapted to hold the localization wire in the tissue mass, the cannula and the localization wire being configured such that each of the at least one anchor remains completely contained in the cannula when the cannula is in the insertion position prior to the cannula being moved to the retracted position; and
an actuator comprising a keyway and a spring located within the hollow interior and extending between the end and the collar, the spring configured for operation between a charged condition where the key and the keyway are unaligned and a discharged condition when the key and the keyway are aligned; wherein
the actuator further comprises a trigger for controlling the operation of the spring, the trigger being operable between a ready position and a release position such that a rotation of the trigger from the ready position to the release position aligns the key and the keyway to thereby release the spring from the charged condition to the discharged condition and move the cannula from the insertion position to the retracted position.

28. The apparatus of claim 27 wherein the actuator retracts the cannula relative to the localization wire from the insertion position to the retracted position to effect the relative movement of the cannula and localization wire and expose the distal end of the localization wire.

29. The apparatus of claim 28 wherein the actuator is configured to automatically effect the relative movement between the cannula and the localization wire.

30. The apparatus of claim 27, wherein the trigger is pivotally mounted to the handle and includes a finger that abuts the collar when the trigger is in the ready position, and can be rotated to the release position to remove the finger from abutting contact with the collar to release the spring.

31. The apparatus of claim 27, wherein the trigger forms the keyway and displacement of the trigger to the release position aligns the key with the keyway to thereby release the spring.

32. The apparatus of claim 27, wherein the localization wire is contained entirely within the cannula and the handle.

33. The apparatus of claim 27 wherein the at least one anchor comprises opposing anchors.

34. The apparatus of claim 27 wherein the at least one anchor is a barb.

35. The apparatus of claim 34 wherein the barb is integrally formed with the localization wire.

36. The apparatus of claim 33 wherein the localization wire comprises an imageable portion.

37. The apparatus of claim 36 wherein the cannula further comprises at least one imageable portion.

38. The apparatus of claim 37 wherein the at least one imageable portion comprises multiple spaced imageable portions.

39. The apparatus of claim 37 wherein the insertion tip is sharpened to aid in the insertion of the cannula into the tissue mass.

40. The apparatus of claim 27, wherein the handle further comprises a base mounting a proximal end of the cannula, and a grip slidably mounted to the base for movement between a first position, where the cannula is substantially received within the grip, and a second position, where the cannula is substantially exteriorly of the grip.

41. The apparatus of claim 40 wherein when the grip is moved to the second position, the actuator is moved to the charged condition.

42. The apparatus of claim 41 wherein the spring is positioned within the grip and extending between the base and the grip, wherein when the grip is in the second position, the spring is in a compressed state.

43. A method of percutaneously implanting a localization wire into a tissue mass, the method comprising:
- providing an apparatus comprising a cannula defining a lumen and having a distal end forming an insertion tip, a collar mounted to the cannula and configured to form a key, a localization wire pre-loaded within the lumen and having a distal end near the insertion tip, and an actuator connected to the cannula and operable between a charged condition when the key and a keyway shaped for receiving the key are unaligned and a discharged condition when the key and the keyway are aligned in order to effect relative movement of the cannula and the localization wire to expose the distal end of the localizing wire;
- completely containing each of the at least one anchor in the lumen of the cannula when actuator is charged and the cannula is in an insertion position prior to the cannula being moved to a retracted position by discharging the actuator;
- inserting the insertion tip of the cannula and the localization wire into the tissue mass while the actuator remains charged; and
- operating the actuator to discharge and retract the cannula to expose the distal end of the localization wire to the tissue mass and expose each of the at least one anchor to the tissue mass without inducing movement of the localization wire, wherein operating the actuator to retract the cannula comprises rotating a trigger to align the key with the keyway thereby releasing the actuator from the charged condition to the discharged condition.

44. The method of claim 43 wherein the act of operating comprises automatically moving the cannula while the localization wire remains stationary.

45. The method of claim 43 wherein the retracting of the cannula further comprises retracting the cannula into an end of a handle with a hollow interior.

46. The method of claim 45 wherein the act of operating comprises removing the cannula from the tissue mass.

47. The method of claim 43 wherein the insertion step further comprises using an imaging system for locating one of the cannula and the localization wire in the tissue mass.

48. The method of claim 47 wherein the act of inserting comprises locating the insertion tip of the cannula at a predetermined location within the tissue mass so that during the act of operating, the localization wire is exposed to the predetermined location.

49. The method of claim 48 wherein the predetermined location is at a biopsy site so that during the act of operating, the localization wire is located at the biopsy site.

50. The method of claim 43 wherein the insertion step comprises positioning an imageable portion on the cannula at a predetermined location within the tissue mass.

51. The method of claim 43 wherein the act of inserting comprises positioning at least one anchor on the localization wire at a predetermined location within the tissue mass so that during the act of operating, the at least one anchor is embedded into the tissue mass at the predetermined location.

52. The method of claim 43 and further comprising positioning an imageable portion of the localization wire at a predetermined location within the tissue mass.

53. The method of claim 52 wherein the predetermined location is at a biopsy site.

54. The method of claim 43 and further comprising a step of moving a handle grip of the apparatus relative to a handle base of the apparatus from a first position, where the cannula is substantially received within the handle grip, to a second position, where the cannula is substantially exteriorly of the handle grip.

* * * * *